(12) United States Patent
Hausch et al.

(10) Patent No.: US 8,962,545 B2
(45) Date of Patent: *Feb. 24, 2015

(54) ENZYME TREATMENT OF FOODSTUFFS FOR CELIAC SPRUE

(75) Inventors: Felix Hausch, Langenselbold (DE); Gary Gray, Stanford, CA (US); Lu Shan, Houston, TX (US); Chaitan Khosla, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 105 days.

This patent is subject to a terminal disclaimer.

(21) Appl. No.: 13/053,120

(22) Filed: Mar. 21, 2011

(65) Prior Publication Data

US 2011/0293724 A1 Dec. 1, 2011

Related U.S. Application Data

(63) Continuation of application No. 11/927,532, filed on Oct. 29, 2007, now Pat. No. 7,910,541, which is a continuation of application No. 10/367,405, filed on Feb. 14, 2003, now Pat. No. 7,303,871.

(60) Provisional application No. 60/357,238, filed on Feb. 14, 2002, provisional application No. 60/380,761, filed on May 14, 2002, provisional application No. 60/392,782, filed on Jun. 28, 2002, provisional application No. 60/422,933, filed on Oct. 31, 2002, provisional application No. 60/428,033, filed on Nov. 20, 2002, provisional application No. 60/435,881, filed on Dec. 20, 2002.

(51) Int. Cl.
| | |
|---|---|
| *C07D 413/12* | (2006.01) |
| *G01N 33/564* | (2006.01) |
| *A61K 38/00* | (2006.01) |
| *A23L 1/03* | (2006.01) |
| *A23L 1/30* | (2006.01) |
| *A61K 31/42* | (2006.01) |
| *A61K 38/48* | (2006.01) |
| *C07D 261/04* | (2006.01) |
| *C07K 14/415* | (2006.01) |
| *C07K 16/16* | (2006.01) |

(52) U.S. Cl.
CPC ............... *C07D 413/12* (2013.01); *A23L 1/034* (2013.01); *A23L 1/30* (2013.01); *A61K 31/42* (2013.01); *A61K 38/4813* (2013.01); *A61K 38/482* (2013.01); *C07D 261/04* (2013.01); *C07K 14/415* (2013.01); *C07K 16/16* (2013.01); *C12Y 304/14005* (2013.01); *C12Y 304/15001* (2013.01); *C12Y 304/21026* (2013.01); *G01N 33/564* (2013.01); *C07K 2317/34* (2013.01); *G01N 2800/202* (2013.01)
USPC ............................ 514/1.1; 530/300; 514/21.3

(58) Field of Classification Search
None
See application file for complete search history.

(56) References Cited

U.S. PATENT DOCUMENTS

| | | | |
|---|---|---|---|
| 4,203,967 A | 5/1980 | Gallo-Torres | |
| 4,656,253 A | 4/1987 | Lewicki | |
| 4,912,120 A | 3/1990 | Castelhano et al. | |
| 4,929,630 A | 5/1990 | Castelhano et al. | |
| 5,208,021 A | 5/1993 | Johnson et al. | |
| 5,372,933 A | 12/1994 | Zamarron et al. | |
| 5,663,304 A | 9/1997 | Builder et al. | |
| 5,716,794 A | 2/1998 | Tjota | |
| 5,766,897 A | 6/1998 | Braxton | |
| 5,789,180 A | 8/1998 | Bernardin | |
| 5,811,098 A | 9/1998 | Plowman et al. | |
| 5,817,523 A | 10/1998 | Picarelli | |
| 5,834,428 A | 11/1998 | Drucker | |
| 5,912,327 A | 6/1999 | Li et al. | |
| 6,165,746 A | 12/2000 | Heitzmann et al. | |
| 6,197,356 B1 * | 3/2001 | Girsh ........................... | 426/312 |
| 6,294,320 B1 | 9/2001 | Hruska et al. | |
| 6,319,726 B1 | 11/2001 | Schuppan et al. | |
| 6,319,756 B2 | 11/2001 | Duesman et al. | |
| 6,395,889 B1 | 5/2002 | Robison | |
| 6,410,550 B1 | 6/2002 | Coe et al. | |
| 6,492,498 B1 | 12/2002 | Vallera et al. | |
| 6,593,106 B1 | 7/2003 | Vicik | |
| 6,610,479 B1 | 8/2003 | Lundeberg et al. | |
| 6,635,462 B1 | 10/2003 | Ensor et al. | |
| 6,642,036 B2 | 11/2003 | Flint et al. | |
| 6,645,739 B2 | 11/2003 | Clark | |
| 6,667,160 B2 | 12/2003 | Fine | |
| 6,833,447 B1 | 12/2004 | Goldman et al. | |
| 6,903,246 B2 | 6/2005 | Gallie | |
| 6,962,989 B1 | 11/2005 | Pompejus et al. | |
| 7,112,660 B1 | 9/2006 | Domingues et al. | |
| 7,144,569 B1 | 12/2006 | Anderson et al. | |
| 7,202,216 B2 | 4/2007 | Sollid et al. | |

(Continued)

FOREIGN PATENT DOCUMENTS

| | | |
|---|---|---|
| DE | 262999 | 12/1988 |
| EP | 0237082 A2 | 9/1987 |

(Continued)

OTHER PUBLICATIONS

Lion (Flavobacterium meningosepticum. Genbank Accession #/EMBL #: D10980. Aug. 1, 1992. (http://www.infobiogen.fr/srs71bin/wgetz?-id+4jqa61Mc9PO+[uniprot-ID:PPCE_FLAMR]+-e.)*

(Continued)

*Primary Examiner* — Maury Audet
(74) *Attorney, Agent, or Firm* — Bozicevic, Field & Francis LLP; Pamela J. Sherwood

(57) ABSTRACT

Administering an effective dose of glutenase to a Celiac or dermatitis herpetiformis patient reduces levels of toxic gluten oligopeptides, thereby attenuating or eliminating the damaging effects of gluten.

19 Claims, 8 Drawing Sheets

(56) References Cited

U.S. PATENT DOCUMENTS

| | | | |
|---|---|---|---|
| 7,265,093 B2 | 9/2007 | Khosla et al. | |
| 7,303,871 B2 * | 12/2007 | Hausch et al. | 435/6.18 |
| 7,320,788 B2 * | 1/2008 | Shan et al. | 424/94.6 |
| 7,442,370 B2 | 10/2008 | Sah et al. | |
| 7,462,688 B2 | 12/2008 | Khosla et al. | |
| 7,521,427 B2 | 4/2009 | Powers et al. | |
| 7,534,426 B2 | 5/2009 | Piper et al. | |
| 7,579,313 B2 | 8/2009 | Khosla et al. | |
| 7,605,150 B2 | 10/2009 | Khosla et al. | |
| 7,651,848 B2 | 1/2010 | Schlegl | |
| 7,696,338 B2 | 4/2010 | Neville, Jr. et al. | |
| 7,910,541 B2 * | 3/2011 | Hausch et al. | 514/1.1 |
| 7,923,532 B2 * | 4/2011 | Hausch et al. | 530/327 |
| 7,928,056 B2 * | 4/2011 | Hausch et al. | 514/1.1 |
| 7,943,312 B2 * | 5/2011 | Hausch et al. | 424/94.64 |
| 2001/0007690 A1 | 7/2001 | Girsh | |
| 2001/0036639 A1 | 11/2001 | Fine | |
| 2002/0018763 A1 | 2/2002 | Zsebo et al. | |
| 2002/0039599 A1 | 4/2002 | Lin et al. | |
| 2002/0076834 A1 | 6/2002 | Detlef et al. | |
| 2003/0215438 A1 | 11/2003 | Hausch et al. | |
| 2003/0224476 A1 | 12/2003 | Chou | |
| 2004/0167069 A1 | 8/2004 | Khosla et al. | |
| 2004/0241664 A1 * | 12/2004 | Dekker et al. | 435/6 |
| 2004/0265298 A1 | 12/2004 | Lin | |
| 2005/0031603 A1 | 2/2005 | Hubertus de Jong et al. | |
| 2005/0049064 A1 | 3/2005 | Gagne | |
| 2005/0090653 A1 | 4/2005 | Klaveness et al. | |
| 2005/0176932 A1 | 8/2005 | Buus et al. | |
| 2005/0227920 A1 | 10/2005 | Lin | |
| 2005/0244823 A1 | 11/2005 | Drijfhout et al. | |
| 2006/0052308 A1 | 3/2006 | Khosla et al. | |
| 2006/0178299 A1 | 8/2006 | Anderson et al. | |
| 2006/0240475 A1 | 10/2006 | Khosla et al. | |
| 2007/0082369 A1 | 4/2007 | Best et al. | |
| 2007/0099238 A1 | 5/2007 | Sigalas et al. | |
| 2008/0299108 A1 | 12/2008 | Khosla et al. | |
| 2008/0311161 A1 | 12/2008 | Gass | |
| 2009/0156490 A1 | 6/2009 | Khosla et al. | |
| 2009/0220554 A1 | 9/2009 | Griffin et al. | |
| 2009/0304754 A1 | 12/2009 | Robic | |

FOREIGN PATENT DOCUMENTS

| | | |
|---|---|---|
| EP | 0905518 A1 | 3/1999 |
| IE | 1490723 | 11/1977 |
| WO | WO 9426774 A1 | 11/1994 |
| WO | WO 9610034 A2 | 4/1996 |
| WO | 99/56698 | 11/1999 |
| WO | WO 0042213 A1 | 7/2000 |
| WO | WO 0125793 A2 | 4/2001 |
| WO | 02/46381 | 6/2002 |
| WO | WO 0283722 * | 10/2002 |
| WO | WO 03068170 A2 | 8/2003 |
| WO | WO 03096984 A2 | 11/2003 |
| WO | WO 03104273 A2 | 12/2003 |
| WO | WO 2004045392 A2 | 6/2004 |
| WO | WO 2005049064 A1 | 6/2005 |
| WO | WO 2008115411 A1 | 9/2008 |
| WO | WO 2008115428 A2 | 9/2008 |
| WO | WO 2010021752 A1 | 2/2010 |
| WO | WO 2010042203 A1 | 4/2010 |

OTHER PUBLICATIONS

Shan L, Molberg Ø, Parrot I, Hausch F, Filiz F, et al. (2002) Structural basis for gluten intolerance in celiac sprue. Science 297: 2275-2279 (also cited in Mitea et al.).*

Mitea et al. A Universal Approach to Eliminate Antigenic Properties of Alpha-Gliadin Peptides in Celiac Disease. PLoS One 5(12): e15637. doi:10.1371/journal.pone.0015637. Dec. 16, 2010. http://www.plosone.org/article/citationList.action?articleURI=info%3Adoi%2F10.1371%2Fjournal.pone.0015637.*

Sjostrom et al. "Identification of a Gliadin T-Cell Epitope in Coeliac Disease: General Importance of Gliadin Deamidation for Intestinal T-Cell Recognition," Scandinavian Journal of Immunology, Aug. 1998 , pp. 111-115(5), vol. 48, No. 2.

Smith; et al., "Abnormal expression of dipeptidylpeptidase IV activity in enterocyte brush-border membranes of children suffering from coeliac disease," Experimental Physiology, Jul. 1990, 75(4):613-616.

Stepniak, D., et al., "Highly efficient gluten degradation with a newly identified prolyl endoprotease: implications for celiac disease," (2006) Am J Physiol Gastrointest Liver Physiol, 291:G621-G629.

Sturgess et al., "Wheat peptide challenge in coeliac disease," The Lancet (1994), 343:758-761.

Vader et al. "The Gluten Response in Children with Celiac Sprue Disease is Directed Toward Multiple Gliadin and Glutenin Peptides," Gastroenterology, 2002, pp. 1729-1737, vol. 122.

Vader et al. "The HLA-DQ2 Gene Dose Effect in Celiac Disease is Doirectly Related to the Magnitude and Breadth of Gluten-Specific T Cell Responses," PNAS, Oct. 14, 2003, pp. 12390-12395, vol. 123, No. 3.

Watts; et al., "Structure-activity relationship analysis of the selective inhibition of transglutaminase 2 by dihydroisoxazoles," Journal of Medicinal Chemistry (2006), 49(25):7493-7501.

Wieser, "The Precipitating Factor in Coeliac Disease," Baillieres Clinical Gastroenterol, 1995, pp. 191-207, vol. 9, Issue 2.

Wieser, "Relation Between Structure An Dcoeliac Toxicity," Acta Paediatr Suppl., 1996, pp. 3-9, vol. 412.

Wruble, Milton, "Enteric Coating. I. A Laboratory Method for the Study and Control of Enteric Coatings," Journal of the American Pharmaceutical Association, Jul. 1935, XXIV(7):570-574.

Xia; et al., "Equilibrium and kinetic analysis of the unusual binding behavior of a highly immunogenic gluten peptide to HLA-DQ2," Biochemistry (2005), 44(11):4442-4449.

Yoshimoto et al., "Prolyl Endopeptidase From Flavobacterium Meningosepticum: Cloning and Sequencing of The Enzyme Gene," J. Biochem., 1991, pp. 873-8, vol. 110.

Zhang et al. "Identification of differentially expressed proteins in human glioblastoma cell lines and tumors," Glia., Apr. 15 2003, pp. 194-208, vol. 42, Issue 2.

"Novosphingobium capsulatum gene for prolyl oligopeptidase, complete cds", GenBank: AB010298.1 (Jan. 2006).

Ahnen et al., "Intestinal aminooligopeptidase. In vivo synthesis on intracellular membranes of rat jejunum," J. Biol. Chem., 1982, pp. 12129-12135, vol. 257.

Arentz-Hansen et al. "Celiac Lesion T Cells Recognizes Epitopes that Cluster in Regions of Gliadins Rich in Proline Residues," Gastroenterology, 2002, pp. 803-809, vol. 123, No. 3.

Arentz-Hansen et al., "The Intestinal T Cell Response to a—Gliadin in Adult Celiac Disease Is Focused on a Single Deamidated Glutamine Targeted by Tissue Transglutaminase," J. Exp. Med., 2000, pp. 603-612, vol. 191.

Arentz-Hansen, et al. "Production of a Panel of Recombinant Gliadins for the Characterisation of T Cell Reactivity in Coeliac Disease," Gut., (2000) 46(1):46-51.

Auger; et al., "Solid-State 13C NMR Study of a Transglutaminase-Inhibitor Adduct," Biochemistry (1993), 32:3930-3934.

Bethune, et al. "Heterologous expression, purification, refolding, and structural-functionalcharacterization of EP-B2, a self-activating barley cysteine endoprotease," (2006) Chemistry & Biology, 13:637-647.

Bordusa et al., "The Specificity of Prolyl Endopeptidase From *Flavobacterium* Meningoseptum: Mapping The S' Subsites by Positional Scanning Via Acyl Transfer," Bioorg. Med. Chem., 1998, pp. 1775-1780, vol. 6.

Campbell, Monoclonal Antibody Technology Section 1.3.4, pp. 1-32, (1984) Elsevier Science Publishers.

Castelhano et al., "Synthesis, Chemistry, and Absolute Configuratin of Novel Transglutaminiase Inhibitors Containing a 3-Halo-4,5-dihydroisoxazole," Bioorg. Chem., 1988, pp. 335-340, vol. 16.

Choi et al. "Chemistry and Biology of Dihydroisoxazole Derivatives: Selectives Inhibitors of Human Transglutaminase 2," Chem. & Biol., 2005, pp. 469-475, vol. 12.

(56) References Cited

OTHER PUBLICATIONS

Colot et al. "The Genes Encoding Wheat Storage Proteins: Towards a Molecular Understanding of Bread-Making Quality and Its Genetic Manipulation," Genet Eng, 1990, pp. 225-241, vol. 12.
Cornell; et al., "In vitro mucosal digestion of synthetic gliadin-derived peptides in celiac disease," Journal of Protein Chemistry (1995), 14(5):335-339.
Database Derwent, Acc-No. 1996-329479, JP-08151396A, "HLA-binding oligopeptide and an immuno: regulator contg, it-used in the treatment of auto: immune diseases," Abstract, Jun. 11, 1996.
de Ritis G. et al. "In Vitro (organ culture) Studies of the Toxicity of Specific A-Gliadin Peptides in celiac Disease," Gastroenbterology, 1988, pp. 41-49, vol. 94.
Frazer et al. "Gluten-induced enteropathy: the effect of partially digested gluten," Lancet, Sep. 5, 1959, pp. 252-255, vol. 2.
Freund, K., et al. "Transglutaminase Inhibition by 2-[(2-Oxopropyl)thio]imidazolium Derivatives: Mechanism of Factor XIIIa Inactivation," 1994 Biochemistry 33:10109-10119.
Garcia-Maroto, et al. "Nucleotide Sequence of a cDNA Encoding an Alpha/Beta-Type Gliadin from Hexaploid Wheat (*Triticum aestivum*)," Plant Molecular Biol., (1990) 14(5):867-868.
Gass et al., "Effect of Barley Endoprotease EP-B2 on Gluten Digestion in the Intact Rat," The Journal of Pharmacology and Experimental Therapeutics (2006), vol. 318, No. 3, pp. 1178-1186.
Goldsmith; et al., "Inhibition of Human Epidermal Transglutaminases In-Vitro and In-Vivo by Tyrosineamidomethyldihydrohaloisoxazoles," Journal of Investigative Dermatology (1991), 97(1):156-158.
Greenberg, C. et al. "Transglutaminases: multifunctional cross-linking enzymes that stabilize tissues," FASEB J., 1991, pp. 3071-3077, vol. 5.
Hartmann, G., et al., "Rapid degradation of gliadin peptides toxic for coeliac disease patients by proteases from germinating cereals," (2006) 44368-371.
Hausch et al. "Design, synthesis, and evaluation of gluten peptide analogs as selective inhibitors of human tissue transglutaminase," Chem Biol., Mar. 2003, pp. 225-231, vol. 10, Issue 3.
Hausch et al., "Intestinal digestive resistance of immunodominant gliadin peptides", Am J Physl Gastrointest Liver Physiol (2002), 283:G996-G1003.
Hitomi, K., et al. "GTP, an Inhibitor of Transglutaminases, is Hydrolyzed by Tissue-Type Transglutaminase (Tgase 2) but Not by Epidermal-Type Transglutaminase (TGase 3)," Biosci. Biotechnol Biochem. 2000 pp. 657-659 vol. 64 Issue 3.
Karpuj et al. "Prolonged survival and decreased abnormal movements in transgenic model of Huntington disease, with administration of the transglutaminase inhibitor cystamine," Nature Med., Feb. 2002, pp. 143-149, vol. 8, Issue 2.
Keillor, J. "Tissue Transglutaminase Inhibition," Chem. & Biol., 2005, pp. 410-412, vol. 12.
Killackey; et al., "A New Class of Mechanism-Based Inhibitors of Translutaminase Enzymes Inhibits the Formation of Cross-Linked Envelopes by Human Malignant Keratinocytes," Molecular Pharmacology (1989), 35(5):701-706.
Kim et al. "Transglutaminases in disease," Neurochem. Int, 2002, pp. 85-103, vol. 40.
Lahteenoja et al. "Local challenge on oral mucosa with an alpha-gliadin related synthetic peptide in patients with celiac disease," Am. J. Gastroenterol., 2000, pp. 2880, vol. 95.
Lion. *Flavobacterium* meningosepticum. Genbank Accession #/EMBL #: D10980. Aug. 1, 1992. http://www.infobiogen.fr/srs71bin/cgi-bin/wgeh?-id+4jqa61Mc9PO+[uniprot-ID:PPCE_FLAME]+-e.
Lorand et al. "Novel inhibitors against the transglutaminase-catalysed crosslinking of lens proteins," Exp Eye Res., May 1998, pp. 531-536, vol. 66.
Martinet et al. "In vivo transglutaminase type 1 expression in normal lung, preinvasive bronchial lesions, and lung cancer," Am J Respir Cell Mol Biol., Apr. 2003, pp. 428-435, vol. 28, Issue 4.

Messer et al. "Studies on the Mechanism of Destruction of the Toxic Action of Wheat Gluten in Coeliac Disease by Crude Papain," Gut., Aug. 1964, pp. 295-303, vol. 5.papain, Gut, 1964, 5:295-303.
Messer et al."Oral papain in gluten intolerance," Lancet, Nov. 6, 1976, p. 1022, vol. 2, Issue 7993.
Moodie, P. "Traditional Baking Enzymes-Proteases," Presented at the American Institute of Baking, Manhattan, Kansas, May 7, 2001 by Peter Moodie, Director—Sales & Marketing, Enzyme Development Corporation, Enzyme Development Corporation.
Nägele, et al. "[Analysis of Food and Feed by Partial Sequences of Characteristic Protein Components (Carrier Peptides). 1 Isolation and Structural Determination of Wheat-Specific Peptides from Chymotryptic Hydrolysates of Gliadin]," (1991), 192(5):415-421.
Online-Medical Dictionary. "Amino acid". Http://cancerweb.ncl.ac.uk./cgi-bin/omd?query=amino+acid. Nov. 13, 1997.
Parrot; et al., "Circular dichroism and nuclear magnetic resonance spectroscopic analysis of immunogenic gluten peptides and their analogs," Journal of Biological Chemistry (2002), 277(47):45572-45578.
Piper et al., "High selectivity of human tissue transglutaminase for immunoactive gliadin peptides: implications for celiac spure," Biochemistry, Jan. 8, 2002, pp. 386-393, vol. 41, Issue 1.
Piper, J., et al., "Effect of prolyl endopeptidase on digestive-resistant gliadin peptide in vivo," The Journal of Pharmacology and Experimental Therapeutics (2004), 311(1):213-219.
Qiao; et al., "Antigen presentation to celiac lesion-derived T cells of a 33-mer gliadin peptide naturally formed by gastrointestinal digestion," Journal of Immunology (2004), 173(3):1757-1762.
Rudolph, R. et al., "In vitro refolding of inclusion body proteins," The FASEB Journal (Jan. 1996), vol. 10, pp. 49-56.
Sárdy, M. et al. "Epidermal transglutaminase (TGase 3) is the autoantigen of dermatitis herpetiformis," J. Exp. Med., 2002, pp. 747-757, vol. 195, Issue 6.
Schuppan et al. "Special Reports and Reviews: Current Concepts of Celiac Disease Pathogenesis," Gastroenterology, 2000, pp. 234-242, vol. 119.
Schuppan; et al., "A Molecular Warhead and its Target Tissue Transglutaminase and Celiac Sprue," Chemistry & Biology (2003), 10(3)1 99-201.
Shan, L. et al. "Structural Basis for Gluten Intolerance in Celiac Sprue," Science 2002, pp. 2275-2279, vol. 297.
Shan, L. et al. "Comparative biochemical analysis of three bacterial prolyl endopeptidases: implications of coeliac sprue," Biochem J, 2004, pp. 311-318, vol. 383.
Siegel et al., "Rational Design of Combination Enzyme Therapy for Celiac Sprue," Chemistry & Biology (Jun. 2006), vol. 13, pp. 649-658.
Siegel; et al., "Transglutaminase 2 inhibitors and their therapeutic role in disease states," Pharmacology & Therapeutics (2007), 115:232-245.
Gass; et al., "Combination Enzyme Therapy for Gastric Digestion of Dietary Gluten in Patients with Celiac Sprue", Gastroenterology (Aug. 2007), 133(2):472-480.
Pliura; et al., "Irreversible inhibition of transglutaminases by sulfonium methylketones: optimization of specificity and potency with -aminoacyl spacers", Journal of Enzyme Inhibition (1992), 6(3):181-94 (abstract).
Rohloff; et al., "Bromonitrile oxide [3+2] cycloadditions in water", Tetrahedron Letters (1992), 33(22):3113-16 (abstract).
Di Cagno; et al., "Proteolysis by Sourdough Lactic Acid Bacteria: Effects on Wheat Flour Protein Fractions and Gliadin Peptides Involved in Human Cereal Intolerance", Applied and Environmental Microbiology (2002), 68 (2):623-633.
Kleinbaum; et al., "New Views on Influencing Celiac Disease by Dietary Measures", International Meeting on Problems on Cereal Processing and Cereal Chemistry (1975), 7:75-83.
Krainick; et al., "Further Studies on the Harmful Effects of Wheat Flour in Celiac Disease, 2. The effect of the enzymatic degradation products of gliadin", Helvetica Paediatrica Acta (1959), 9:124-140.
Simpson, "Proteolytic degradation of cereal prolamins—the problems with proline", Plant Science (2001), 161:825-838.
O'Farrelly; et al., "(alpha) Gliadin antibody levels: a serological test for coeliac disease", Clinical Research (Jun. 1983), 286:2007-2010.

(56) References Cited

OTHER PUBLICATIONS

Hadjivassiliou; et al., "Autoantibody targeting of brain and intestinal transglutaminase in gluten ataxia", Neurology (Feb. 2006), 66:373-377.

Hadjivassiliou; et al., "Neuropathy associated with gluten sensitivity", J. Neurol. Neurosurg. Psychiatry (Jul. 2006), 77:1262-1266.

Maki; et al., "Coeliac disease", Lancet (Jun. 1997), 349:1755-1759.

* cited by examiner

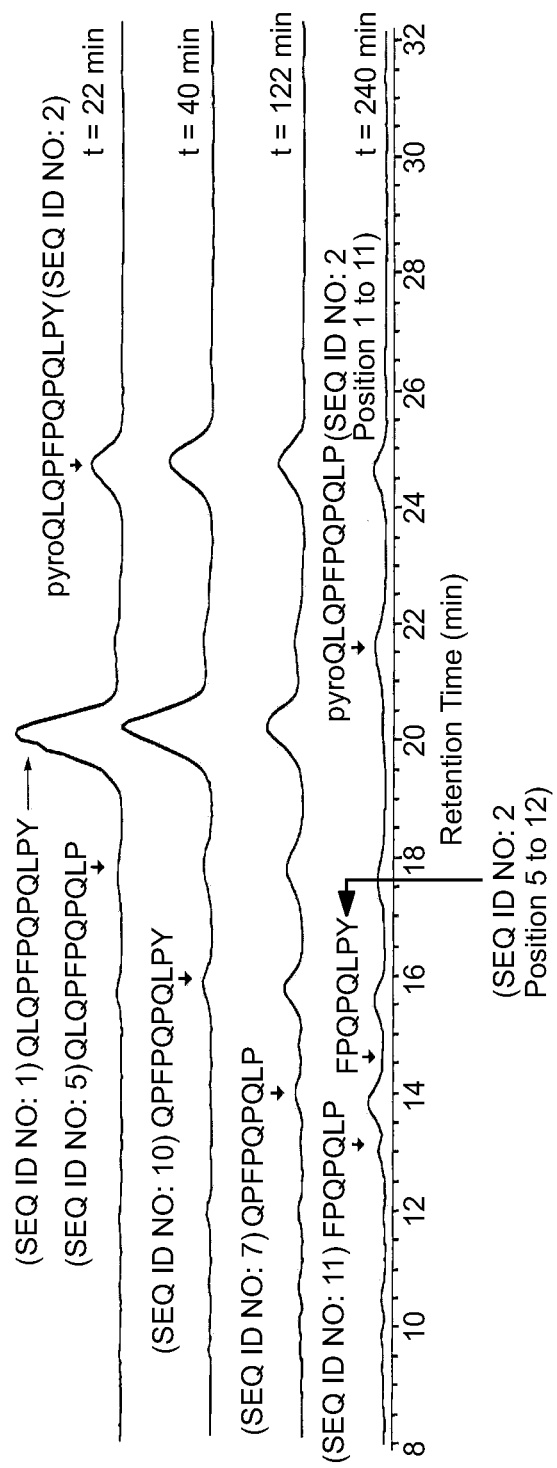

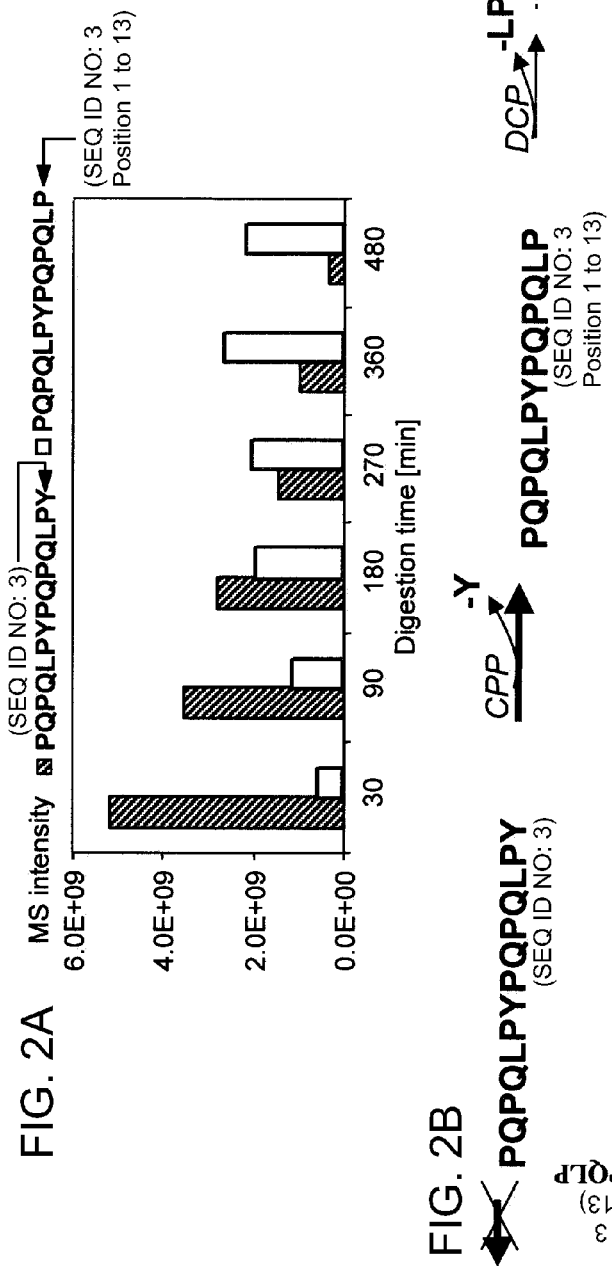
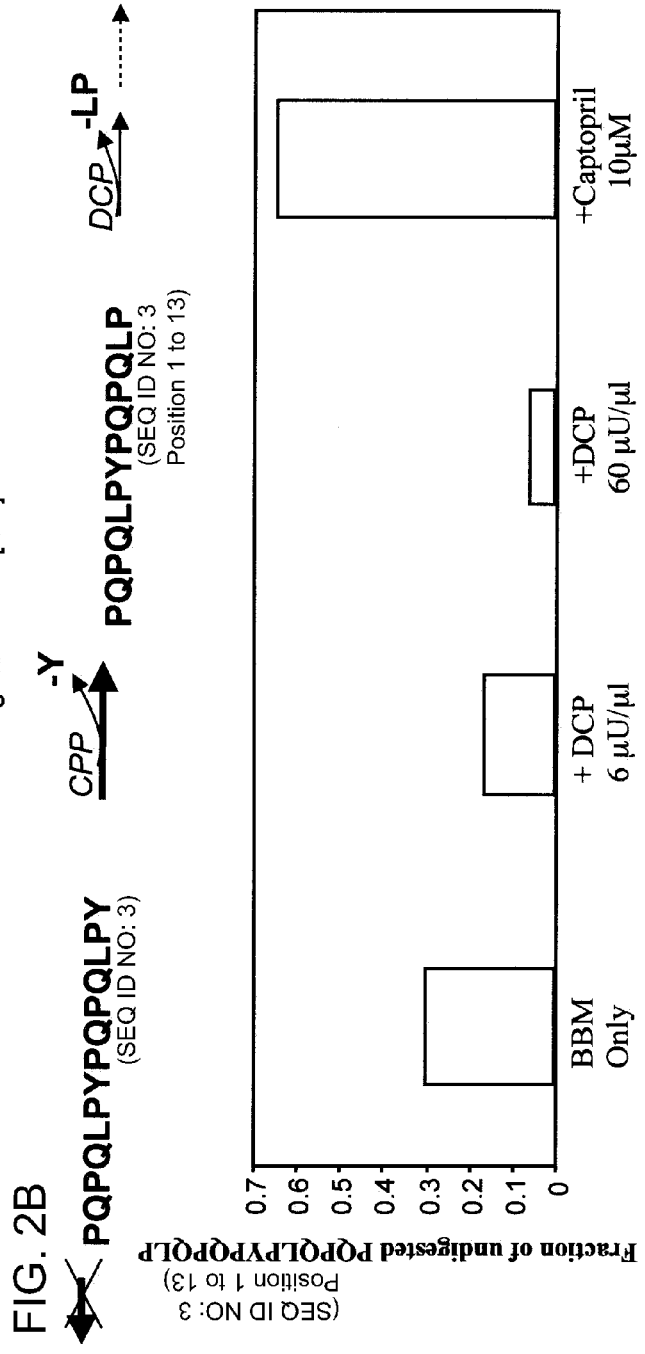
FIG. 2A
FIG. 2B

ENZYME TREATMENT OF FOODSTUFFS FOR CELIAC SPRUE

GOVERNMENT SUPPORT

This invention was made with Government support under contract 9910949 awarded by the National Science Foundation. The Government has certain right in this invention.

BACKGROUND OF THE INVENTION

In 1953, it was first recognized that ingestion of gluten, a common dietary protein present in wheat, barley and rye causes disease in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac Sprue is generally considered to be an autoimmune disease and the antibodies found in the serum of the patients supports a theory of an immunological nature of the disease. Antibodies to tissue transglutaminase (tTG) and gliadin appear in almost 100% of the patients with active Celiac Sprue, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villus atrophy of the small intestine.

At the present time there is no good therapy for the disease, except to completely avoid all foods containing gluten. Although gluten withdrawal has transformed the prognosis for children and substantially improved it for adults, some people still die of the disease, mainly adults who had severe disease at the outset. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac Sprue, improved methods of treating or ameliorating the effects of the disease are needed. The present invention addresses such needs.

SUMMARY OF THE INVENTION

The present invention provides methods for treating the symptoms of Celiac Sprue and/or dermatitis herpetiformis by decreasing the levels of toxic gluten oligopeptides in foodstuffs, either prior to or after ingestion by a patient. The present invention relates to the discovery that certain gluten oligopeptides resistant to cleavage by gastric and pancreatic enzymes, that the presence of such peptides results in toxic effects, and that enzymatic treatment can remove such peptides and their toxic effects. By digestion with glutenases, these toxic oligopeptides are cleaved into fragments, thereby preventing or relieving their toxic effects in Celiac Sprue or dermatitis herpetiformis patients. In one aspect of the invention, a foodstuff is treated with a glutenase prior to consumption by the patient. In another aspect of the invention, a glutenase is administered to a patient and acts internally to destroy the toxic oligopeptides. In another aspect of the invention, a recombinant organism that produces a glutenase is administered to a patient. In another aspect of the invention, gene therapy is used to provide the patient with a gene that expresses a glutenase that destroys the toxic oligopeptides.

In one aspect, the invention provides methods for the administration of enteric formulations of one or more glutenases, each of which may be present as a single agent or a combination of active agents. In another aspect of the invention, stabilized forms of glutenases are administered to the patient, which stabilized forms are resistant to digestion in the stomach, e.g. to acidic conditions. Alternative methods of administration include genetic modification of patient cells, e.g. enterocytes, to express increased levels of peptidases capable of cleaving immunogenic oligopeptides of gliadin; pretreatment of foods with glutenases; the introduction of micro-organisms expressing such peptidases so as to transiently or permanently colonize the patient intestinal tract; and the like.

In another aspect, the invention provides pharmaceutical formulations containing one or more glutenases and a pharmaceutically acceptable carrier. Such formulations include formulations in which the glutenase is contained within an enteric coating that allows delivery of the active agent to the intestine and formulations in which the active agents are stabilized to resist digestion in acidic stomach conditions. The formulation may comprise one or more glutenases or a mixture or "cocktail" of agents having different activities.

In another aspect, the invention provides foodstuffs derived from gluten-containing foods that have been treated to remove or to reduce to non-toxic levels the gluten-derived oligopeptides that are toxic to Celiac Sprue patients, and methods for treating foods to hydrolyze toxic gluten oligopeptides. In other aspects, the invention provides recombinant microorganisms useful in hydrolyzing the gluten-derived oligopeptides that are toxic to Celiac Sprue patients from foodstuffs; methods for producing glutenases that digest the gluten-derived oligopeptides that are toxic to Celiac Sprue patents; purified preparations of the glutenases that digest the gluten-derived oligopeptides that are toxic to Celiac Sprue patents; and recombinant vectors that code for the expression of glutenases that digest the gluten-derived oligopeptides that are toxic to Celiac Sprue patents.

These and other aspects and embodiments of the invention are described in more detail below.

BRIEF DESCRIPTION OF THE DRAWINGS

FIGS. 1A-1B. Brush border membrane catalyzed digestion of the immunodominant gliadin peptide. FIG. 1A: LC-MS traces of peptides as shown, after digestion with 27 ng/μl rat brush border membrane (BBM) protein for the indicated time. Reaction products were separated by reversed phase HPLC and detected by mass spectroscopy (ion counts m/z=300-2000 g/mol). The indicated peptide fragments were confirmed by characteristic tandem MS fragmentation patterns. The SEQ ID NO:2 pyroQLQPFPQPQLPY peak corresponds to an N-terminally pyroglutaminated species, which is generated during HPLC purification of the synthetic starting material. FIG. 1B: Abundance of individual digestion products as a function of time. The peptide fragments in FIG. 1A were quantified by integrating the corresponding MS peak area (m/z=300-2000 g/mol). The resulting MS intensities are plotted as a function of digestion time (with BBM only). The digestion experiment was repeated in the presence of exogenous DPP IV from *Aspergillus fumigatus* (Chemicon International, CA, 0.28 μU DPP IV/ng BBM protein) and analyzed as above (open bars). The relative abundance of different intermediates could be estimated from the UV$_{280}$ traces and control experiments using authentic standards. The inserted scheme shows an interpretative diagram of the digestion pathways of SEQ ID NO:1) QLQPFPQPQLPY and its intermediates, the BBM peptidases involved in each step, and the amino acid residues that are released. The preferred breakdown pathway is indicated in bold. APN=aminopeptidase N, CPP=carboxypeptidase P, DPP IV=dipeptidyl dipeptidase IV.

FIG. 2A-2B. C-terminal digestion of the immunodominant gliadin peptide by brush border membrane. FIG. 2A: (SEQ ID NO:3) PQPQLPYPQPQLPY was digested by 27 ng/μl brush border membrane (BBM) protein preparations for the indicated time and analyzed as in FIG. 1A. The identity of the starting material and the product (SEQ ID NO:4) PQPQLPYPQPQLP was corroborated by MSMS fragmentation. The intrinsic mass intensities of the two peptides were identical, and the UV$_{280}$ extinction coefficient of (SEQ ID NO:4) PQPQLPYPQPQLP was half of the starting material in accordance with the loss of one tyrosine. All other intermediates were ≤1%. The scheme below shows the proposed BBM digestion pathway of (SEQ ID NO:3) PQPQLPYPQPQLPY with no observed N-terminal processing (crossed arrow) and the removal of the C-terminal tyrosine by carboxypeptidase P(CPP) in bold. Further C-terminal processing by dipeptidyl carboxypeptidase (DCP) was too slow to permit analysis of the subsequent digestion steps (dotted arrows). FIG. 2B: Influence of dipeptidyl carboxypeptidase on C-terminal digestion. (SEQ ID NO:3) PQPQLPYPQPQLPY in phosphate buffered saline:Tris buffered saline=9:1 was digested by BBM alone or with addition of exogenous rabbit lung DCP (Cortex Biochemicals, CA) or captopril. After overnight incubation, the fraction of accumulated SEQ ID NO:4) PQPQLPYPQPQLP (compared to initial amounts of (SEQ ID NO:3) PQPQLPYPQPQLPY at t=0 min) was analyzed as in FIG. 2A, but with an acetonitrile gradient of 20-65% in 6-35 minutes.

DETAILED DESCRIPTION OF THE EMBODIMENTS

Figure 1B:
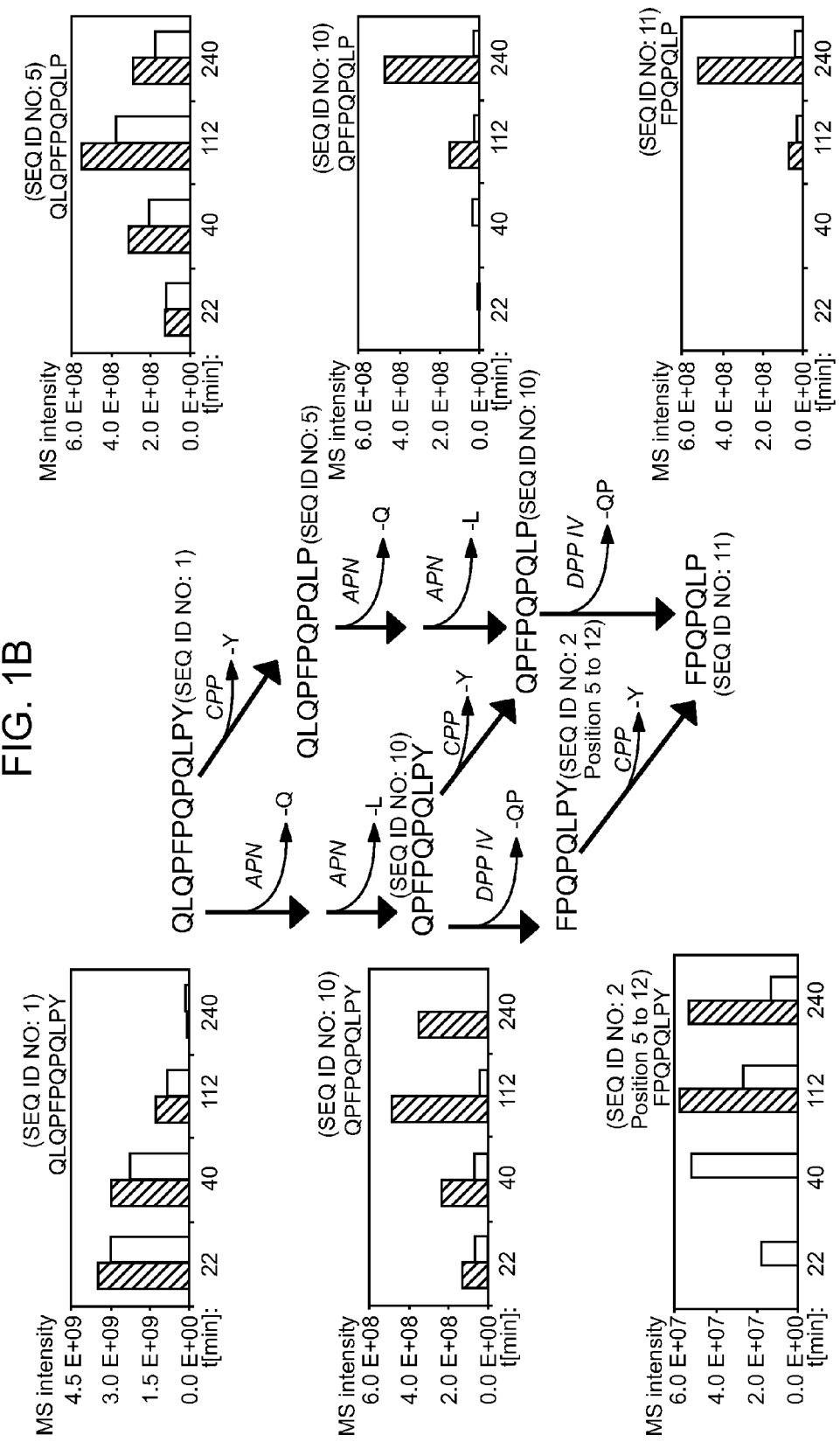

Celiac Sprue and/or dermatitis herpetiformis are treated by digestion of gluten oligopeptides contained in foodstuffs consumed by individuals suffering from one or both conditions. Gluten oligopeptides are highly resistant to cleavage by gastric and pancreatic peptidases such as pepsin, trypsin, chymotrypsin, and the like. By providing for digestion of gluten oligopeptides with glutenase, oligopeptides are cleaved into fragments, thereby preventing the disease-causing toxicity.

Methods and compositions are provided for the administration of one or more glutenases inhibitors to a patient suffering from Celiac Sprue and/or dermatitis herpetiformis. In some patients, these methods and compositions will allow the patient to ingest glutens without serious health consequences, much the same as individuals that do not suffer from either of these conditions. In some embodiments, the formulations of the invention comprise a glutenase contained in an enteric coating that allows delivery of the active agent(s) to the intestine; in other embodiments, the active agent(s) is stabilized to resist digestion in acidic stomach conditions. In some cases the active agent(s) have hydrolytic activity under acidic pH conditions, and can therefore initiate the proteolytic process on toxic gluten sequences in the stomach itself. Alternative methods of administration provided by the invention include genetic modification of patient cells, e.g. enterocytes, to express increased levels of glutenases; and the introduction of micro-organisms expressing such glutenases so as to transiently or permanently colonize the patient's intestinal tract. Such modified patient cells (which include cells that are not derived from the patient but that are not immunologically rejected when administered to the patient) and microorganisms of the invention are, in some embodiments, formulated in a pharmaceutically acceptable excipient, or introduced in foods. In another embodiment, the invention provides foods pretreated or combined with a glutenase and methods for treating foods to remove the toxic oligopeptides of gluten.

The methods of the invention can be used for prophylactic as well as therapeutic purposes. As used herein, the term "treating" refers both to the prevention of disease and the treatment of a disease or a pre-existing condition. The invention provides a significant advance in the treatment of ongoing disease, to stabilize or improve the clinical symptoms of the patient. Such treatment is desirably performed prior to loss of function in the affected tissues but can also help to restore lost function or prevent further loss of function. Evidence of therapeutic effect may be any diminution in the severity of disease, particularly as measured by the severity of symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like.

Patients that can benefit from the present invention may be of any age and include adults and children. Children in particular benefit from prophylactic treatment, as prevention of early exposure to toxic gluten peptides can prevent initial development of the disease. Children suitable for prophylaxis can be identified by genetic testing for predisposition, e.g. by HLA typing; by family history, by T cell assay, or by other medical means. As is known in the art, dosages may be adjusted for pediatric use.

Although the present invention is not to be bound by any theory of action, it is believed that the primary event in Celiac Sprue requires certain gluten oligopeptides to access antigen binding sites within the lamina propria region interior to the relatively impermeable surface intestinal epithelial layer. Ordinarily, oligopeptide end products of pancreatic protease processing are rapidly and efficiently hydrolyzed into amino acids and/or di- or tri-peptides by gastric peptidases before they are transported across the epithelial layer. However, glutens are particularly peptidase resistant, which may be attributed to the usually high proline content of these proteins, a residue that is inaccessible to most gastric peptidases.

The normal assimilation of dietary proteins by the human gut can be divided into three major phases: (i) initiation of proteolysis in the stomach by pepsin and highly efficient endo- and C-terminal cleavage in the upper small intestine cavity (duodenum) by secreted pancreatic proteases and carboxypeptidases; (ii) further processing of the resulting oligopeptide fragments by exo- and endopeptidases anchored in the brush border surface membrane of the upper small intestinal epithelium (jejunum); and (iii) facilitated transport of the resulting amino acids, di- and tripeptides across the epithelial cells into the lamina propria, from where these nutrients enter capillaries for distribution throughout the body. Because most proteases and peptidases normally present in the human stomach and small intestine are unable to hydrolyze the amide bonds of proline residues, it is shown herein that the abundance of proline residues in gliadins and related proteins from wheat, rye and barley can constitute a major digestive obstacle for the enzymes involved in phases (i) and (ii) above. This leads to an increased concentration of relatively stable gluten derived oligopeptides in the gut. Furthermore, because aminopeptidase and especially carboxypeptidase activity towards oligopeptides with proline residues at the N- and C-termini, respectively, is low in the small intestine, detoxification of gluten oligopeptides in phase (iii) above is also slow. By administering peptidases capable of cleaving such gluten oligopeptides in accordance with the methods of the invention, the amount of toxic peptides is diminished, thereby slowing or blocking disease progression.

Tissue transglutaminase (tTGase), an enzyme found on the extracellular surface in many organs including the intestine, catalyzes the formation of isopeptide bonds between glutamine and lysine residues of different polypeptides, leading to protein-protein crosslinks in the extracellular matrix. The enzyme tTGase is the primary focus of the autoantibody response in Celiac Sprue. Gliadins, secalins and hordeins contain several sequences rich in Pro-Gln residues that are high-affinity substrates for tTGase; tTGase catalyzed deamidation of at least some of these sequences dramatically increases their affinity for HLA-DQ2, the class II MHC allele present in >90% Celiac Sprue patients. Presentation of these deamidated epitopes by DQ2 positive antigen presenting cells effectively stimulates proliferation of gliadin-specific T cells from intestinal biopsies of most Celiac Sprue patients. The toxic effects of gluten include immunogenicity of the gluten oligopeptides, leading to inflammation; the lectin theory predicts that gliadin peptides may also directly bind to surface receptors.

The present invention relates generally to methods and reagents useful in treating foodstuffs containing gluten with enzymes that digest the oligopeptides toxic to Celiac Sprue patients. Although specific enzymes are exemplified herein, any of a number of alternative enzymes and methods apparent to those of skill in the art upon contemplation of this disclosure are equally applicable and suitable for use in practicing the invention. The methods of the invention, as well as tests to determine their efficacy in a particular patient or application, can be carried out in accordance with the teachings herein using procedures standard in the art. Thus, the practice of the present invention may employ conventional techniques of molecular biology (including recombinant techniques), microbiology, cell biology, biochemistry and immunology within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991); as well as updated or revised editions of all of the foregoing.

As used herein, the term "glutenase" refers to an enzyme useful in the methods of the present invention that is capable, alone or in combination with endogenous or exogenously added enzymes, of cleaving toxic oligopeptides of gluten proteins of wheat, barley, oats and rye into non-toxic fragments. Gluten is the protein fraction in cereal dough, which can be subdivided into glutenins and prolamines, which are subclassified as gliadins, secalins, hordeins, and avenins from wheat, rye, barley and oat, respectively. For further discussion of gluten proteins, see the review by Wieser (1996) Acta Paediatr Suppl. 412:3-9, incorporated herein by reference.

In one embodiment, the term "glutenase" as used herein refers to a protease or a peptidase enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "protease" or "peptidase" can refer to a glutenase and as used herein describe a protein or fragment thereof with the capability of cleaving peptide bonds, where the scissile peptide bond may either be terminal or internal in oligopeptides or larger proteins. Prolyl-specific peptidases are glutenases useful in the practice of the present invention.

Glutenases of the invention include protease and peptidase enzymes having at least about 20% sequence identity at the amino acid level, more usually at least about 40% sequence identity, and preferably at least about 70% sequence identity to one of the following peptidases: prolyl endopeptidase (PEP) from *F. meningosepticum* (Genbank accession number D10980), PEP from *A. hydrophila* (Genbank accession number D14005), PEP form *S. caplsulata* (Genbank accession number AB010298), DCP I from rabbit (Genbank accession number X62551), DPP IV from *Aspergillus fumigatus* (Genbank accession number U87950) or cysteine proteinase B from *Hordeum vulgare* (Genbank accession number JQ1110).

In one embodiment of the present invention, the glutenase is a PEP. Homology-based identification (for example, by a PILEUP sequence analysis) of prolyl endopeptidases can be routinely performed by those of skill in the art upon contemplation of this disclosure to identify PEPs suitable for use in the methods of the present invention. PEPs are produced in microorganisms, plants and animals. PEPs belong to the serine protease superfamily of enzymes and have a conserved catalytic triad composed of a Ser, His, and Asp residues. Some of these homologs have been characterized, e.g. the enzymes from *F. meningoscepticum, Aeromonas hydrophila, Aeromonas punctata, Novosphingobium capsulatum, Pyrococcus furiosus* and from mammalian sources are biochemically characterized PEPs. Others such as the Nostoc and *Arabidopsis* enzymes are likely to be PEPs but have not been fully characterized to date. Yet others, such as the *E. coli* and *M. xanthus* enzymes, may not be PEPs but are homologous members of the serine protease superfamily, and can be useful starting materials in protein engineering to make a PEP useful in the practice of the present invention. Relative to the *F. meningoscepticum* enzyme, the pairwise sequence identity of this family of enzymes is in the 30-60% range. Accordingly, PEPs include enzymes having >30% identity to the *F. meningoscepticum* enzyme (as in the *Pyrococcus* enzymes), or having >40% identity (as in the *Novosphingobium* enzymes), or having >50% identity (as in the *Aeromonas* enzymes) to the *F. meningoscepticum* enzyme.

A glutenase of the invention includes a peptidase or protease that has a specific activity of at least 2.5 U/mg, preferably 25 U/mg and more preferably 250 U/mg for cleavage of a peptide comprising one of more of the following motifs: Gly-Pro-pNA, Z-Gly-Pro-pNA (where Z is a benzyloxycarbonyl group), and Hip-His-Leu, where "Hip" is hippuric acid, pNA is para-nitroanilide, and 1 U is the amount of enzyme required to catalyze the turnover of 1 mole of substrate per minute.

A glutenase of the invention includes an enzyme belonging to any of the following enzyme classifications: EC 3.4.21.26, EC 3.4.14.5, or EC 3.4.15.1.

A glutenase of the invention includes an enzyme having a kcat/Km of at least about 2.5 s–1 M–1, usually at least about 250 s–1 M–1 and preferably at least about 25000 s–1 M–1 for cleavage of any of the following peptides under optimal conditions: (SEQ ID NO:1) QLQPFPQPQLPY, (SEQ ID NO:3) PQPQLPYPQPQLPY, (SEQ ID NO:13) QPQQSFPQQQ, (SEQ ID NO:14) QLQPFPQPELPY, (SEQ ID NO:15) PQPELPYPQPELPY, (SEQ ID NO:16) QPQQSFPEQQ. A glutenase of the invention includes peptidase or protease having a specificity kcat/Km>2 mM$^{-1}$s$^{-1}$ for the quenched fluorogenic substrate Abz-QPQQP-Tyr(NO$_2$)-D.

A glutenase useful in the practice of the present invention can be identified by its ability to cleave a pretreated substrate to remove toxic gluten oligopeptides, where a "pretreated substrate" is a gliadin, hordein, secalin or avenin protein that has been treated with physiological quantities of gastric and pancreatic proteases, including pepsin (1:100 mass ratio), trypsin (1:100), chymotrypsin (1:100), elastase (1:500), and carboxypeptidases A and B (1:100). Pepsin digestion may be performed at pH 2 for 20 min., to mimic gastric digestion, followed by further treatment of the reaction mixture with trypsin, chymotrypsin, elastase and carboxypeptidase at pH 7 for 1 hour, to mimic duodenal digestion by secreted pancreatic enzymes. The pretreated substrate comprises oligopeptides resistant to digestion, e.g. under physiological conditions.

The ability of a peptidase or protease to cleave a pretreated substrate can be determined by measuring the ability of an enzyme to increase the concentration of free NH$_2$-termini in a reaction mixture containing 1 mg/ml pretreated substrate and 10 g/ml of the peptidase or protease, incubated at 37° C. for 1 hour. A glutenase useful in the practice of the present invention will increase the concentration of the free amino termini under such conditions, usually by at least about 25%, more usually by at least about 50%, and preferably by at least about 100%. A glutenase includes an enzyme capable of reducing the residual molar concentration of oligopeptides greater than about 1000 Da in a 1 mg/ml "pretreated substrate" after a 1 hour incubation with 10 µg/ml of the enzyme by at least about 2-fold, usually by at least about 5-fold, and preferably by at least about 10-fold. The concentration of such oligopeptides can be estimated by methods known in the art, for example size exclusion chromatography and the like.

A glutenase of the invention includes an enzyme capable of reducing the potency by which a "pretreated substrate" can antagonize binding of (SEQ ID NO:17) PQPELPYPQPQLP to HLA-DQ2. The ability of a substrate to bind to HLA-DQ is indicative of its toxicity; fragments smaller than about 8 amino acids are generally not stably bound to Class II MHC. Treatment with a glutenase that digests toxic oligopeptides, by reducing the concentration of the toxic oligopeptides, prevents a mixture containing them from competing with a test peptide for MHC binding. To test whether a candidate glutenase can be used for purposes of the present invention, a 1 mg/ml solution of "pretreated substrate" may be first incubated with 10 µg/ml of the candidate glutenase, and the ability of the resulting solution to displace radioactive (SEQ ID NO:18) PQPELPYPQPQLP pre-bound to HLA-DQ2 molecules can then be quantified, with a reduction of displacement, relative to a non-treated control, indicative of utility in the methods of the present invention.

A glutenase of the invention includes an enzyme that reduces the anti-tTG antibody response to a "gluten challenge diet" in a Celiac Sprue patient by at least about 2-fold, more usually by at least about 5-fold, and preferably by at least about 10-fold. A "gluten challenge diet" is defined as the intake of 100 g bread per day for 3 days by an adult Celiac Sprue patient previously on a gluten-free diet. The anti-tTG antibody response can be measured in peripheral blood using standard clinical diagnostic procedures, as known in the art.

Excluded from the term "glutenase" are the following peptidases: human pepsin, human trypsin, human chymotrypsin, human elastase, papaya papain, and pineapple bromelain, and usually excluded are enzymes having greater than 98% sequence identity at the amino acid level to such peptidases, more usually excluded are enzymes having greater than 90% sequence identity at the amino acid level to such peptidases, and preferably excluded are enzymes having greater than 70% sequence identity at the amino acid level to such peptidases.

Among gluten proteins with potential harmful effect to Celiac Sprue patients are included the storage proteins of wheat, species of which include *Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi*; etc. A review of the genes encoding wheat storage proteins may be found in Colot (1990) *Genet Eng* (NY) 12:225-41. Gliadin is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be identified using routine methods of molecular biology. In one aspect of the present invention, genetically modified plants are provided that differ from their naturally occurring counterparts by having gliadin proteins that contain a reduced content of glutamine and proline residues.

Examples of gliadin sequences include but are not limited to wheat alpha gliadin sequences, for example as provided in Genbank, accession numbers AJ133612; AJ 133611; AJ133610; AJ133609; AJ 133608; AJ133607; AJ133606; AJ133605; AJ133604; AJ 133603; AJ133602; D84341.1; U51307; U51306; U51304; U51303; U50984; and U08287. A sequence of wheat omega gliadin is set forth in Genbank accession number AF280605.

For the purposes of the present invention, toxic gliadin oligopeptides are peptides derived during normal human digestion of gliadins and related storage proteins as described above, from dietary cereals, e.g. wheat, rye, barley, and the like. Such oligopeptides are believed to act as antigens for T cells in Celiac Sprue. For binding to Class II MHC proteins, immunogenic peptides are usually from about 8 to 20 amino acids in length, more usually from about 10 to 18 amino acids. Such peptides may include PXP motifs, such as the motif PQPQLP (SEQ ID NO:8). Determination of whether an oligopeptide is immunogenic for a particular patient is readily determined by standard T cell activation and other assays known to those of skill in the art.

As demonstrated herein, during digestion, peptidase resistant oligopeptides remain after exposure of glutens, e.g. gliadin, to normal digestive enzymes. Examples of peptidase resistant oligopeptides are provided, for example, as set forth in SEQ ID NO:5, 6, 7 and 10. Other examples of immunogenic gliadin oligopeptides are described in Wieser (1995) Baillieres Clin Gastroenterol 9(2):191-207, incorporated herein by reference.

Determination of whether a candidate enzyme will digest a toxic gluten oligopeptide, as discussed above, can be empirically determined. For example, a candidate may be combined with an oligopeptide comprising one or more Gly-Pro-pNA, Z-Gly-Pro-pNA, Hip-His-Leu, Abz-QLP-Tyr($NO_2$)-PQ, Abz-PYPQPQ-Tyr($NO_2$), PQP-Lys(Abz)-LP-Tyr($NO_2$)-PQPQLP, PQPQLP-Tyr($NO_2$)-PQP-Lys(Abz)-LP motifs; with one or more of the oligopeptides (SEQ ID NO:1) QLQPFPQPQLPY, (SEQ ID NO:3) PQPQLPYPQPQLPY, (SEQ ID NO:13) QPQQSFPQQQ, (SEQ ID NO:14) QLQPFPQPELPY, (SEQ ID NO:15) PQPELPYPQPELPY, (SEQ ID NO:16) QPQQSFPEQQ or (SEQ ID NO:12) LQLQPFPQPQLPYPQPQLPYPQPQLPYPQPQPF; or with a pretreated substrate comprising one or more of gliadin, hordein, secalin or avenin proteins that have been treated with physiological quantities of gastric and pancreatic proteases. In each instance, the candidate is determined to be a glutenase of the invention if it is capable of cleaving the oligopeptide. Glutenases that have a low toxicity for human cells and are active in the physiologic conditions present in the intestinal brush border are preferred for use in some applications of the invention, and therefore it may be useful to screen for such properties in candidate glutenases.

The oligopeptide or protein substrates for such assays may be prepared in accordance with conventional techniques, such as synthesis, recombinant techniques, isolation from natural sources, or the like. For example, solid-phase peptide synthesis involves the successive addition of amino acids to create a linear peptide chain (see Merrifield (1963) J. Am. Chem. Soc. 85:2149-2154). Recombinant DNA technology can also be used to produce the peptide.

Candidate glutenases for use in the practice of the present invention can be obtained from a wide variety of sources, including libraries of natural and synthetic proteins. For example, numerous means are available for random and directed mutation of proteins. Alternatively, libraries of natural proteins in the form of bacterial, fungal, plant and animal extracts are available or readily produced. Extracts of germinating wheat and other grasses is of interest as a source of candidate enzymes. Natural or synthetically produced libraries and compounds are readily modified through conventional chemical, physical and biochemical means, and such means can be used to produce combinatorial libraries. Known pharmacological agents may be subjected to directed or random chemical modifications, such as acylation, alkylation, esterification, and amidification, to produce structural analogs of proteins.

Generally, a variety of assay mixtures are run in parallel with different peptidase concentrations to obtain a differential response to the various concentrations. Typically, one of these concentrations serves as a negative control, i.e. at zero concentration or below the level of detection. A variety of other reagents may be included in a screening assay. These include reagents like salts, detergents, and the like that are used to facilitate optimal activity and/or reduce non-specific or background interactions. Reagents that improve the efficiency of the assay may be used. The mixture of components is added in any order that provides for the requisite activity. Incubations are performed at any suitable temperature, typically between 4 and 40° C. Incubation periods are selected for optimum activity but can also be optimized to facilitate rapid high-throughput screening or other purposes. Typically, between 0.1 and 1 hours will be sufficient.

The level of digestion of the toxic oligopeptide can be compared to a baseline value. The disappearance of the starting material and/or the presence of digestion products can be monitored by conventional methods. For example, a detectable marker can be conjugated to a peptide, and the change in molecular weight associated with the marker is then determined, e.g. acid precipitation, molecular weight exclusion, and the like. The baseline value can be a value for a control sample or a statistical value that is representative a control population. Various controls can be conducted to ensure that an observed activity is authentic, including running parallel reactions, positive and negative controls, dose response, and the like.

Active glutenases identified by the screening methods described herein can serve as lead compounds for the synthesis of analog compounds to identify glutenases with improved properties. Identification of analog compounds can be performed through use of techniques such as self-consistent field (SCF) analysis, configuration interaction (CI) analysis, and normal mode dynamics analysis.

In one embodiment of the invention, the glutenase is a prolyl endopeptidase (PEP, EC 3.4.21.26). Prolyl endopeptidases are widely distributed in microorganisms, plants and animals, and have been cloned from *Flavobacterium meningosepticum*, (Yoshimoto et al. (1991) *J. Biochem.* 110, 873-8); *Aeromonas hydrophyla* (Kanatani et al. (1993) *J. Biochem.* 113, 790-6); *Sphingomonas capsulata* (Kabashima et al. (1998) *Arch. Biochem. Biophys.* 358, 141-148), *Pyrococcus furious* (Robinson et al. (1995) *Gene* 152, 103-6); pig (Rennex et al. (1991) *Biochemistry* 30, 2195-2030); and the like. The suitability of a particular enzyme is readily determined by the assays described above, by clinical testing, determination of stability in formulations, and the like. Other sources of PEP include *Lactobacilli* (Habibi-Najafi et al. (1994) J. Dairy Sci. 77, 385-392), from where the gene of interest can be readily cloned based on sequence homology to the above PEP's or via standard reverse genetic procedures involving purification, amino-acid sequencing, reverse translation, and cloning of the gene encoding the target extracellular enzyme.

In another embodiment of the invention, glutenases are peptidases present in the brush border, which are supplemented. Formulations of interest may comprise such enzymes in combination with other peptidases. Peptidases present in brush border include dipeptidyl peptidase IV (DPP IV, EC 3.4.14.5), and dipeptidyl carboxypeptidase (DCP, EC 3.4.15.1). The human form of these proteins may be used, or modified forms may be isolated from other suitable sources. Example of DPP IV enzymes include *Aspergillus* spp. (e.g. Byun et al. (2001) J. Agric. Food Chem. 49, 2061-2063), ruminant bacteria such as *Prevotella albensis* M384 (NCBI protein database Locus #CAC42932), dental bacteria such as *Porphyromonas gingivalis* W83 (Kumugai et al. (2000) Infect. Immun. 68, 716-724), lactobacilli such as *Lactobacillus helveticus* (e.g. Vesanto, et al, (1995) Microbiol. 141, 3067-3075), and *Lactococcus lactis* (Mayo et al., (1991) Appl. Environ. Microbiol. 57, 38-44). Other DPP IV candidates can readily be recognized based on homology to the above enzymes, preferably >30% sequence identity. Similarly, secreted dipeptidyl carboxypeptidases that cleave C-terminal X-Pro sequences are found in many microbial sources including *Pseudomonas* spp (e.g. Ogasawara et al, (1997) Biosci. Biotechnol. Biochem. 61, 858-863), *Streptomyces* spp. (e.g. Miyoshi et al., (1992) J. Biochem. 112, 253-257) and *Aspergilli* spp. (e.g. Ichishima et al., (1977) J. Biochem. 81, 1733-1737). Of particular interest is the enzyme from *Aspergillus saitoi* (Ichishima), due to its high activity at acidic pH values. Although the genes encoding many of these enzymes have not yet been cloned, they can be readily cloned by standard reverse genetic procedures. The DCP I enzymes can be purified from the extracellular medium based on their ability to hydrolyze (SEQ ID NO:19) Z-Gly-Pro-Leu-Gly-Pro, Z-Gly-Pro, or Hip-Gly-Pro. Alternatively, putative DCP I genes can be identified based on homology to the *E. coli* enzyme (NCBI protein database Locus CAA41014.)

In another embodiment of the invention, glutenases are endoproteases found in developing grains of toxic cereals such as wheat, barley and rye. For example, Dominguez and Cejudo (Plant Physiol. 112, 1211-1217, 1996) have shown that the endosperm of wheat (i.e. the part of the grain that contains gliadin and glutenin) contains a variety of neutral and acid proteases. Although these proteases have not been individually characterized, they are expected to be an especially rich source of glutenases. Moreover, although the genes encoding these proteases have not yet been cloned, Dominguez and Cejudo have established a convenient SDS-PAGE assay for identification and separation of these proteases. After excision of the corresponding protein bands from the gel, limited sequence information can be obtained. The cDNA encoding these proteases can therefore be readily cloned from this information using established reverse genetic procedures, and expressed in heterologous bacterial or fungal hosts. Of particular interest are proteases that hydrolyze α2-gliadin within the 33-mer amino acid sequence identified in Example 2 below. Of further interest are the subset of these proteases that retain activity at acidic pH values (pH2-5) encountered in the stomach.

The amino acid sequence of a glutenase, e.g. a naturally occurring glutenase, can be altered in various ways known in the art to generate targeted changes in sequence and additional glutenase enzymes useful in the formulations and compositions of the invention. Such variants will typically be functionally-preserved variants, which differ, usually in sequence, from the corresponding native or parent protein but still retain the desired biological activity. Variants also include fragments of a glutenase that retain enzymatic activity. Various methods known in the art can be used to generate targeted changes, e.g. phage display in combination with random and targeted mutations, introduction of scanning mutations, and the like.

A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine).

Glutenase fragments of interest include fragments of at least about 20 contiguous amino acids, more usually at least about 50 contiguous amino acids, and may comprise 100 or more amino acids, up to the complete protein, and may extend further to comprise additional sequences. In each case, the key criterion is whether the fragment retains the ability to digest the toxic oligopeptides that contribute to the symptoms of Celiac Sprue.

Modifications of interest that do not alter primary sequence include chemical derivatization of proteins, e.g., acetylation or carboxylation. Also included are modifications of glycosylation, e.g. those made by modifying the glycosylation patterns of a protein during its synthesis and processing or in further processing steps; e.g. by exposing the protein to enzymes that affect glycosylation, such as mammalian glycosylating or deglycosylating enzymes. Also embraced are sequences that have phosphorylated amino acid residues, e.g. phosphotyrosine, phosphoserine, or phosphothreonine.

Also useful in the practice of the present invention are proteins that have been modified using molecular biological techniques and/or chemistry so as to improve their resistance to proteolytic degradation and/or to acidic conditions such as those found in the stomach, and to optimize solubility properties or to render them more suitable as a therapeutic agent. For example, the backbone of the peptidase can be cyclized to enhance stability (see Friedler et al. (2000) *J. Biol. Chem.* 275:23783-23789). Analogs of such proteins include those containing residues other than naturally occurring L-amino acids, e.g. D-amino acids or non-naturally occurring synthetic amino acids.

The glutenase proteins of the present invention may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. Using synthesizers, one can readily substitute for the naturally occurring amino acids one or more unnatural amino acids. The particular sequence and the manner of preparation will be determined by convenience, economics, purity required, and the like. If desired, various groups can be introduced into the protein during synthesis that allow for linking to other molecules or to a surface. For example, cysteines can be used to make thioethers, histidines can be used for linking to a metal ion complex, carboxyl groups can be used for forming amides or esters, amino groups can be used for forming amides, and the like.

The glutenase proteins useful in the practice of the present invention may also be isolated and purified in accordance with conventional methods from recombinant production systems and from natural sources. A lysate can be prepared from the expression host and the lysate purified using HPLC, exclusion chromatography, gel electrophoresis, affinity chromatography, and/or other purification techniques. Typically, the compositions used in the practice of the invention will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one aspect, the present invention provides a purified preparation of a glutenase. Prior to the present invention, there was no need for a glutenase that could be ingested by a human or mixed with a foodstuff. Thus, prior to the present invention most glutenases did not exist in a form free of contaminants that could be deleterious to a human if ingested. The present invention creates a need for such glutenase preparations and provides them and methods for preparing them. In a related embodiment, the present invention provides novel foodstuffs that are derived from gluten-containing foodstuffs but have been treated to reduce the concentration and amount of the oligopeptides and oligopeptide sequences discovered to be toxic to Celiac Sprue patients. While gluten-free or reduced-gluten content foods have been made, the foodstuffs of the present invention differ from such foodstuffs not only by the manner in which they are prepared, by treatment of the foodstuff with a glutenase, but also by their content, as the methods of the prior art result in alteration of non-toxic (to Celiac Sprue patients) components of the foodstuff, resulting in a different taste and composition. Prior art foodstuffs include, for example, Codex Alimentarius wheat starch, which is available in Europe and has <100 ppm gluten. The starch is usually prepared by processes that take advantage of the fact that gluten is insoluble in water whereas starch is soluble.

In one embodiment of the present invention, a Celiac Sprue patient is, in addition to being provided a glutenase or food treated in accordance with the present methods, provided an inhibitor of tissue transglutaminase, an anti-inflammatory agent, an anti-ulcer agent, a mast cell-stabilizing agents, and/or and an-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

As used herein, compounds which are "commercially available" may be obtained from commercial sources including but not limited to Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

Compounds useful for co-administration with the glutenases and treated foodstuffs of the invention can also be made by methods known to one of ordinary skill in the art. As used herein, "methods known to one of ordinary skill in the art" may be identified though various reference books and databases. Suitable reference books and treatises that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

The glutenase proteins of the invention and/or the compounds administered therewith are incorporated into a variety of formulations for therapeutic administration. In one aspect, the agents are formulated into pharmaceutical compositions by combination with appropriate, pharmaceutically acceptable carriers or diluents, and are formulated into preparations in solid, semi-solid, liquid or gaseous forms, such as tablets, capsules, powders, granules, ointments, solutions, suppositories, injections, inhalants, gels, microspheres, and aerosols. As such, administration of the glutenase and/or other compounds can be achieved in various ways, usually by oral administration. The glutenase and/or other compounds may be systemic after administration or may be localized by virtue of the formulation, or by the use of an implant that acts to retain the active dose at the site of implantation.

In pharmaceutical dosage forms, the glutenase and/or other compounds may be administered in the form of their pharmaceutically acceptable salts, or they may also be used alone or in appropriate association, as well as in combination with other pharmaceutically active compounds. The agents may be combined, as previously described, to provide a cocktail of activities. The following methods and excipients are exemplary and are not to be construed as limiting the invention.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71(3):307-18.

In another embodiment, a microorganism, for example bacterial or yeast culture, capable of producing glutenase is administered to a patient. Such a culture may be formulated as an enteric capsule; for example, see U.S. Pat. No. 6,008,027, incorporated herein by reference. Alternatively, microorganisms stable to stomach acidity can be administered in a capsule, or admixed with food preparations.

In another embodiment, the glutenase is admixed with food, or used to pre-treat foodstuffs containing glutens. Glutenase present in foods can be enzymatically active prior to or during ingestion, and may be encapsulated or otherwise treated to control the timing of activity. Alternatively, the glutenase may be encapsulated to achieve a timed release after ingestion, e.g. in the intestinal tract.

Formulations are typically provided in a unit dosage form, where the term "unit dosage form," refers to physically discrete units suitable as unitary dosages for human subjects, each unit containing a predetermined quantity of glutenase in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Depending on the patient and condition being treated and on the administration route, the glutenase may be administered in dosages of 0.01 mg to 500 mg/kg body weight per day, e.g. about 20 mg/day for an average person. A typical dose of glutenase in patients will be in at least about 1 mg/adult, more usually at least about 10 mg; and preferably at least about 50 mg; usually not more than about 5 g, more usually not more than about 1 g, and preferably not more than about 500 mg. Dosages will be appropriately adjusted for pediatric formulation. In children the effective dose may be lower, for example at least about 0.1 mg, or 0.5 mg. In combination therapy involving, for example, a PEP+DPP IV or PEP+DCP I, a comparable dose of the two enzymes may be given; however, the ratio will be influenced by the relative stability of the two enzymes toward gastric and duodenal inactivation.

Those of skill will readily appreciate that dose levels can vary as a function of the specific enzyme, the severity of the symptoms and the susceptibility of the subject to side effects.

Some of the glutenases are more potent than others. Preferred dosages for a given enzyme are readily determinable by those of skill in the art by a variety of means. A preferred means is to measure the physiological potency of a given compound.

Other formulations of interest include formulations of DNA encoding glutenases of interest, so as to target intestinal cells for genetic modification. For example, see U.S. Pat. No. 6,258,789, herein incorporated by reference, which discloses the genetic alteration of intestinal epithelial cells.

The methods of the invention are used to treat foods to be consumed or that are consumed by individuals suffering from Celiac Sprue and/or dermatitis herpetiformis by delivering an effective dose of glutenase. If the glutenase is administered directly to a human, then the active agent(s) are contained in a pharmaceutical formulation. Alternatively, the desired effects can be obtained by incorporating glutenase into food products or by administering live organisms that express glutenase, and the like. Diagnosis of suitable patients may utilize a variety of criteria known to those of skill in the art. A quantitative increase in antibodies specific for gliadin, and/or tissue transglutaminase is indicative of the disease. Family histories and the presence of the HLA alleles HLA-DQ2 [DQ(a1*0501, b1*02)] and/or DQ8 [DQ(a1*0301, b1*0302)] are indicative of a susceptibility to the disease.

The therapeutic effect can be measured in terms of clinical outcome or can be determined by immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of a disease.

Various methods for administration may be employed, preferably using oral administration, for example with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

Example 1

Detection of Immunodominant Peptides from Gliadin and Enzymes that Degrade them

The following examples describe the discovery and characterization of a small number of immunodominant peptides from gliadin, which account for most of the stimulatory activity of dietary gluten on intestinal and peripheral T lymphocytes found in Celiac Sprue patients. The proteolytic kinetics of these immunodominant peptides were analyzed at the small intestinal surface. Brush border membrane vesicles from adult rat intestines were used to show that these proline-glutamine-rich peptides are exceptionally resistant to enzymatic processing, and that dipeptidyl peptidase IV and dipeptidyl carboxypeptidase are the rate-limiting enzymes in their digestion. Supplementation of the brush border membrane with trace quantities of a bacterial prolyl endopeptidase leads to rapid destruction of these gliadin peptides. These results provide the basis for enzyme-mediated therapies for treating food for provision to Celiac Sprue patients, and for treating such patients directly that offer distinct advantages over the only current therapeutic option, which is strict exclusion of gluten containing food.

To investigate the digestion of gluten, liquid chromatography coupled mass spectroscopy analysis (LC-MS-MS) was utilized to investigate the pathways and associated kinetics of hydrolysis of immunodominant gliadin peptides treated with rat BBM preparations. Because the rodent is an excellent small animal model for human intestinal structure and function, rat BBM was chosen as a suitable model system for these studies.

BBM fractions were prepared from rat small intestinal mucosa as described in Ahnen et al. (1982) *J. Biol. Chem.* 257, 12129-35. The specific activities of the known BB peptidases were determined to be 127 μU/μg for Aminopeptidase N (APN, EC 3.4.11.2), 60 μU/μg for dipeptidyl peptidase IV (DPP IV, EC 3.4.14.5), and 41 μU/μg for dipeptidyl carboxypeptidase (DCP, EC 3.4.15.1) using standard assays. No proline aminopeptidase (EC 3.4.11.5) or prolyl endopeptidase activity (PEP, EC 3.4.21.26) activity was detectable (<5 μU/μg). Alkaline phosphatase and sucrase were used as control BBM enzymes with activities of 66 μU/μg and 350 U/μg, respectively.

BBM fractions were partially purified from the small intestinal mucosa of adult female rats maintained on an ad libitum diet of wheat-based standard rodent chow. Total protein content was determined by a modified method of Lowry with BSA as a standard. Alkaline phosphatase activity was determined with nitrophenyl phosphate. Sucrase activity was measured using a coupled glucose assay. DPP IV, proline aminopeptidase and APN were assayed continuously at 30° C. in 0.1M Tris-HCl, pH 8.0, containing 1 mM of the p-nitroanilides (=8,800 M-1 cm-1) Gly-Pro-pNA, Pro-pNA or Leu-pNA, the latter in additional 1% DMSO to improve solubility. DCP activity was measured in a 100 μl reaction as the release of hippuric acid from Hip-His-Leu. PEP activity was determined continuously with 0.4 mM Z-Gly-Pro-pNA in PBS: $H_2O$:dioxane (8:1.2:0.8) at 30° C. One unit is the consumption of 1 μmol substrate per minute.

DPP IV and DCP are both up-regulated by a high proline content in the diet. However, APN activity using standard substrates was found to be higher than DPP IV even when fed extreme proline rich diets. Also, although a higher DCP vs. CPP activity has been observed with the model peptide Z-GPLAP at saturating concentrations, a difference in Km values could easily account the reversed ratio measured. The amount of 100 M was chosen as the initial peptide concentration, because non-saturating kinetics (kcat/Km) were considered to be physiologically more relevant than the maximal rates of hydrolysis (kcat).

Proteolysis with the BBM preparation was investigated using the peptide (SEQ ID NO:1) QLQPFPQPQLPY, a product of chymotryptic digestion of α-9 gliadin (Arentz-Hansen et al. (2000) *J. Exp. Med.* 191, 603-12). This peptide has been shown to stimulate proliferation of T cells isolated from most Celiac Sprue patients, and hence is considered to possess an immunodominant epitope. It was subjected to BBM digestion, followed by LC-MS-MS analysis. A standard 50 μl digestion mixture contained 100 μM of synthetic peptide, 10 μM tryptophan and Cbz-tryptophan as internal standards, and resuspended BBM preparations with a final protein content of 27 ng/μl and exogenous proteins, as indicated, in phosphate buffered saline. After incubation at 37° C. for the indicated time, the enzymes were inactivated by heating to 95° C. for 3 minutes. The reaction mixtures were analyzed by LC-MS (SpectraSystem, ThermoFinnigan) using a C18 reversed phase column (Vydac 218TP5215, 2.1×150 mm) with water: acetonitrile:formic acid (0.1%):trifluoroacetic acid (0.025%) as the mobile phase (flow: 0.2 ml/min) and a gradient of 10% acetonitrile for 3 minutes, 10-20% for 3 minutes, 20-25% for 21 minutes followed by a 95% wash. Peptide fragments in the mass range of m/z=300-2000 were detected by electrospray ionization mass spectroscopy using a LCQ ion trap and their identities were confirmed by MSMS fragmentation patterns.

While the parent peptide (SEQ ID NO:1) QLQPFPQPQLPY disappeared with an apparent half life of 35 min, several intermediates were observed to accumulate over prolonged periods (FIG. 1A). The MS intensities (m/z=300-2000 g/mol) and $UV_{280}$ absorbances of the parent peptides (SEQ ID NO:1) QLQPFPQPQLPY and (SEQ ID NO:3) PQPQLPYPQPQLPY were found to depend linearly on concentration in the range of 6-100 μM. The reference peptides (SEQ ID NO:4) PQPQLPYPQPQLP, (SEQ ID NO:5) QLQPFPQPQLP, (SEQ ID NO:6) QPQFPQPQLPY and (SEQ ID NO:7) QPFPQPQLP were generated individually by limited proteolysis of the parent peptides with 10 g/ml carboxypeptidase A (C-0261, Sigma) and/or 5.9 g/ml leucine aminopeptidase (L-5006, Sigma) for 160 min at 37° C. and analyzed by LC-MS as in FIG. 1.

Indeed, the subsequent processing of the peptide was substantially retarded (FIG. 1B). The identities of the major intermediates were confirmed by tandem MS, and suggested an unusually high degree of stability of the (SEQ ID NO:8) PQPQLP sequence, a common motif in T cell stimulating peptides. Based on this data and the known amino acid preferences of the BBM peptidases, the digestive breakdown of (SEQ ID NO:1) QLQPFPQPQLPY was reconstructed, as shown in the insert of FIG. 1B. The preferred pathway involves serial cleavage of the N-terminal glutamine and leucine residues by aminopeptidase N (APN), followed by removal of the C-terminal tyrosine by carboxypeptidase P(CPP) and hydrolysis of the remaining N-terminal QP-dipeptide by DPP IV. As seen in FIG. 1B, the intermediate (SEQ ID NO:6) QPFPQPQLPY (formed by APN attack on the first two N-terminal residues) and its derivatives are increasingly resistant to further hydrolysis. Because the high proline content seemed to be a major cause for this proteolytic resistance, digestion was compared with a commercially available non-proline control peptide (SEQ ID NO:9) RRLIEDNEYTARG (Sigma, St. Louis, Mo.). Initial hydrolysis was much faster ($t_{1/2}$=10 min). More importantly, digestive intermediates were only transiently observed and cleared completely within one hour, reflecting a continuing high specificity of the BBM for the intermediate peptides.

Because the three major intermediate products (SEQ ID NO:10) QPFPQPQLPY, (SEQ ID NO:7) QPFPQPQLP, (SEQ ID NO:11) FPQPQLP) observed during BBM mediated digestion of (SEQ ID NO:1) QLQPFPQPQLPY are substrates for DPP IV, the experiment was repeated in the presence of a 6-fold excess activity of exogenous fungal DPP IV. Whereas the relatively rapid decrease of the parent peptide and the intermediate levels of (SEQ ID NO:5) QLQPFPQPQLP were largely unchanged, the accumulation of DPP IV substrates was entirely suppressed, and complete digestion was observed within four hours. (FIG. 1B, open bars).

To investigate the rate-limiting steps in BBM mediated digestion of gliadin peptides from the C-terminal end, another known immunodominant peptide derived from wheat-gliadin, (SEQ ID NO:3) PQPQLPYPQPQLPY, was used. Although peptides with N-terminal proline residues are unlikely to form in the small intestine (none were observed during BBM digestion of (SEQ ID NO:1) QLQPFPQPQLPY, FIG. 1A), they serve as a useful model for the analysis of C-terminal processing, because the N-terminal end of this peptide can be considered proteolytically inaccessible due to minimal proline aminopeptidase activity in the BBM. As shown in FIG. 2, this peptide is even more stable than (SEQ ID NO:1) QLQPFPQPQLPY. In particular, removal of the C-terminal tyrosine residue by carboxypeptidase P(CPP) is the first event in its breakdown, and more than four times slower than APN activity on (SEQ ID NO:1) QLQPFPQPQLPY (FIG. 1B). The DCP substrate (SEQ ID NO:4) PQPQLPYPQPQLP emerges as a major intermediate following carboxypeptidase P catalysis, and is highly resistant to further digestion, presumably due to the low level of endogenous DCP activity naturally associated with the BBM. To confirm the role of DCP as a rate-limiting enzyme in the C-terminal processing of immunodominant gliadin peptides, the reaction mixtures were supplemented with rabbit lung DCP. Exogenous DCP significantly reduced the accumulation of (SEQ ID NO:4) PQPQLPYPQPQLP after overnight incubation in a dose dependent manner. Conversely, the amount of accumulated (SEQ ID NO:4) PQPQLPYPQPQLP increased more than 2-fold in the presence of 10 μM of captopril, a DCP-specific inhibitor, as compared with unsupplemented BBM.

Together, the above results demonstrate that (i) immunodominant gliadin peptides are exceptionally stable toward breakdown catalyzed by BBM peptidases, and (ii) DPP IV and especially DCP are rate-limiting steps in this breakdown process at the N- and C-terminal ends of the peptides, respectively. Because BBM exopeptidases are restricted to N- or C-terminal processing, it was investigated if generation of additional free peptide ends by pancreatic enzymes would accelerate digestion. Of the pancreatic proteases tested, only elastase at a high (non-physiological) concentration of 100 ng/μl was capable of hydrolyzing (SEQ ID NO:3) PQPQLPYPQPQ↓LPY. No proteolysis was detected with trypsin or chymotrypsin.

Figure 3:
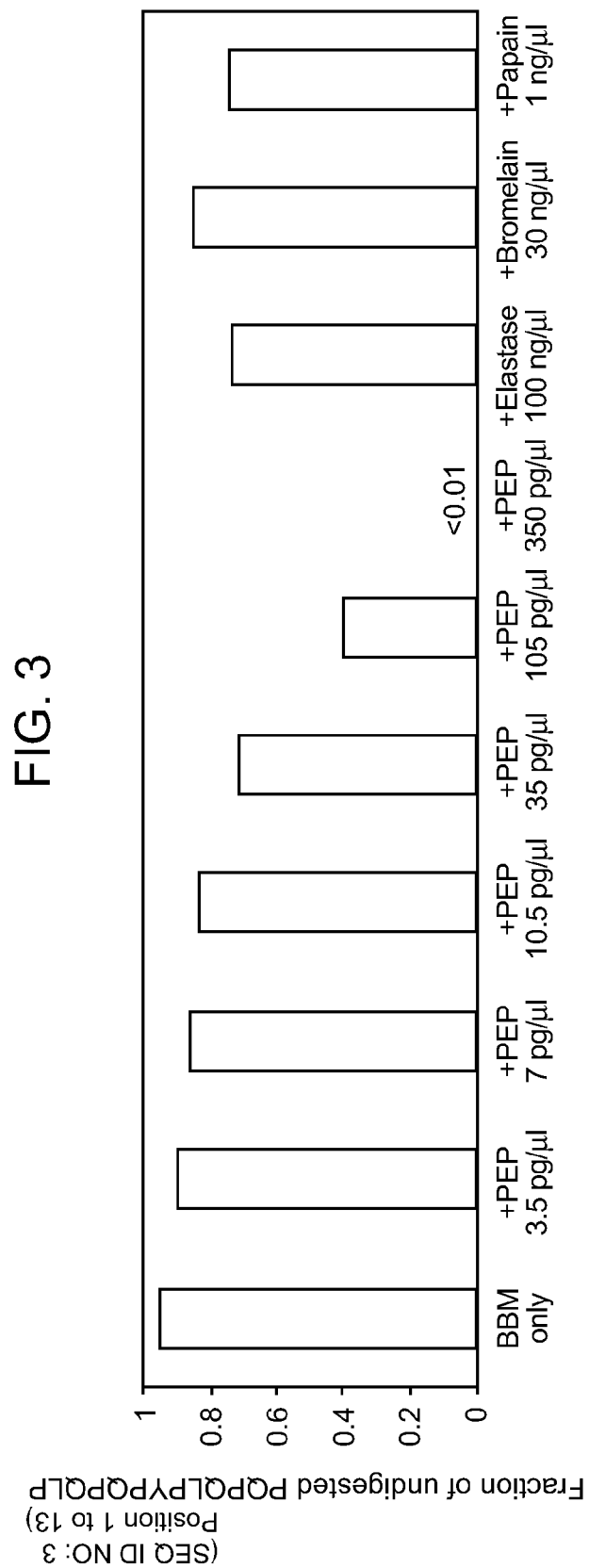
FIG. 3. Dose dependent acceleration of brush border mediated digestion by exogenous endoproteases. As seen from FIG. 2A-2B, the peptide (SEQ ID NO:4) PQPQLPYPQPQLP is stable toward further digestion. This peptide was digested with 27 ng/μl brush border membranes, either alone, with increasing amounts of exogenous prolyl endopeptidase (PEP, specific activity 28 μU/pg) from *Flavobacterium meningosepticum* (US Biological, MA), or with additional elastase (E-1250, Sigma, Mo.), bromelain (B-5144, Sigma, Mo.) or papain (P-5306, Sigma, Mo.) (12). After one hour, the fraction of remaining (SEQ ID NO:4) PQPQLPYPQPQLP (compared to the initial amount at t=0 min) was analyzed and quantified as in FIG. 1.

Alerted by the high proline content as a hallmark of most immunogenic gliadin peptides, a proline-specific endopeptidase was tested for the generation of new, free peptide termini. A literature search on available proteases led to the identification of prolyl endopeptidase (PEP) from *Flavobacterium meningosepticum*, which is specific for the C-terminal cleavage of prolines and readily available from recombinant sources (Yoshimoto et al. (1991) J. Biochem. 110, 873-8). The stable (SEQ ID NO:4) PQPQLPYPQPQLP intermediate was digested with BBM in the presence of exogenous PEP. FIG. 3 shows the dose dependent acceleration of (SEQ ID NO:4) PQPQLPYPQPQLP digestion with increasing PEP concentration. As little as 3.5 pg PEP/27 ng BBM protein was sufficient to double the extent of proteolysis of this gliadin fragment compared to incubation with BBM alone. In comparison, other commonly used proteases like papain, bromelain or porcine elastase were much less efficient, requiring 30-fold (papain) or 3000-fold (bromelain, elastase) higher amounts of enzyme compared to PEP to give similar results. Their proteolysis was restricted to the cleavage of the $Gln^4$-$Leu^5$ and/or $Gln^{11}$-$Leu^{12}$ bonds.

Prolyl endopeptidase (EC 3.4.21.26) had a preference for the Pro8-Gln9 and to a lesser extent the Pro6-Tyr7 bond of the (SEQ ID NO:4) PQPQLP↓YP↓QPQLP peptide. A similar preferential cleavage was found for (SEQ ID NO:1) QLQPFP↓QPQLPY. This is in agreement with the preference of this prolyl endopeptidase for a second proline in the S2' position (Bordusa and Jakubke (1998) Bioorg. Med. Chem. 6, 1775-80). Based on this P↓XP motif and on the present data, up to 16 new, major cleavage sites can be predicted in the α2-gliadin sequence, a major source of immunodominant epitopes identified thus far upon PEP treatment. All of them are located in the critical N-terminal part. The internal cleavage by PEP can be expected to generate additional (otherwise inaccessible) substrates for DPP IV and DCP thereby complementing the natural assimilation process of gliadins by the BBM. Thus, the specificity of prolyl endopeptidase is ideally suited for detoxification of persistent immunoactive gliadin peptides in Celiac Sprue.

The above data demonstrates that proline-rich gliadin peptides are extraordinarily resistant to digestion by small intestinal endo- and exopeptidases, and therefore are likely to accumulate at high concentrations in the intestinal cavity after a gluten rich meal. The pathological implication of digestive resistance is strengthened by the observed close correlation of proline content and celiac toxicity as observed in the various common cereals (Schuppan (2000) *Gastroenterology* 119, 234-42). This analysis of the digestive pathways of immunodominant peptides also provides a mechanism for determining whether enzymes capable of accelerating this exceptionally slow process can be therapeutically useful in the Celiac Sprue diet.

Addition of exogenous DPP IV and DCP can compensate for the intrinsically slow proline processing by the BBM, although both enzymes rely on efficient generation of free N- and C-termini by endoproteolytic cleavage. In a preferred embodiment, a soluble bacterial prolyl endopeptidase (PEP) is used, which was shown to be extremely efficient at hydrolyzing the proline-rich gliadin fragments. Although PEP is expressed in human brain, lung, kidney and intestine, no such activity has been reported in the brush border.

Supplementation of the Celiac Sprue diet with bioavailable PEP (with or without DPP IV and/or DCP), by virtue of facilitating gliadin peptide cleavage to non-toxic and/or digestible fragments, is useful in attenuating or eliminating the inflammatory response to gluten. Such a treatment regimen is analogous to the enzyme therapy treatment used to treat lactose intolerance, where orally administered lactase is effective in cleaving and thereby detoxifying the lactose in milk products. Prolyl endopeptidases are widely distributed in microorganisms, plants and animals and have been cloned from *Aeromonas hydrophyla* (Kanatani et al. (1993) *J. Biochem.* 113, 790-6); *Pyrococcus furious* (Robinson et al. (1995) *Gene* 152, 103-6) and from pig brain (Rennex et al. (1991) *Biochemistry* 30, 2195-2030). These isozymes constitute alternative detoxifying peptidases. Furthermore, the prolyl endopeptidase used in this study is readily amenable to protein engineering by directed evolution. Thus, optimization of PEP specificity towards immunogenic gliadin peptides can be achieved.

Example 2

Further Characterization of Immunodominant Gliadin Peptides and Means for their Digestion It has long been known that the principal toxic components of wheat gluten are a family of closely related Pro-Gln rich proteins called gliadins. Peptides from a short segment of α-gliadin appear to account for most of the gluten-specific recognition by CD4+ T cells from Celiac Sprue patients. These peptides are substrates of tissue transglutaminase (tT-Gase), the primary auto-antigen in Celiac Sprue, and the products of this enzymatic reaction bind to the class II HLA DQ2 molecule. This example describes a combination of in vitro and in vivo animal and human studies used to characterize this "immunodominant" region of α-gliadin as part of an unusually long proteolytic product generated by the digestive process that: (a) is exceptionally resistant to further breakdown by gastric, pancreatic and intestinal brush border proteases; (b) is the highest specificity substrate of human tissue transglutaminase (tTGase) discovered to date; (c) contains at least six overlapping copies of epitopes known to be recognized by patient derived T cells; (d) stimulates representative T cell clones that recognize these epitopes with sub-micromolar efficacy; and (e) has homologs in proteins from all toxic foodgrains but no homologs in non-toxic foodgrain proteins. In aggregate, these findings demonstrate that the onset of symptoms upon gluten exposure in the Celiac Sprue patient can be traced back to a small segment of α-gliadin. Finally, it is shown that this "super-antigenic" long peptide can be detoxified in vitro and in vivo by treatment with bacterial prolyl endopeptidase, providing a peptidase therapy for Celiac Sprue.

Identification of stable peptides from gastric protease, pancreatic protease and brush border membrane peptidase catalyzed digestion of recombinant α2-gliadin: The protein α2-gliadin, a representative α-gliadin (Arentz-Hansen et al. (2000) Gut 46:46), was expressed in recombinant form and purified from *E. coli*. The α2-gliadin gene was cloned in pET28a plasmid (Novagen) and transformed into the expression host BL21(DE3) (Novagen). The transformed cells were grown in 1-liter cultures of LB media containing 50 µg/ml of kanamycin at 37° C. until the OD600 0.6-1 was achieved. The expression of α2-gliadin protein was induced with the addition of 0.4 mM isopropyl β-D-thiogalactoside (Sigma) and the cultures were further incubated at 37° C. for 20 hours. The cells expressing the recombinant α2-gliadin were centrifuged at 3600 rpm for 30 minutes. The pellet was resuspended in 15 ml of disruption buffer (200 mM sodium phosphate; 200 mM NaCl; 2.5 mM DTT; 1.5 mM benzamidine; 2.5 mM EDTA; 2 mg/L pepstatin; 2 mg/L leupeptin; 30% v/v glycerol) and lysed by sonication (1 minute; output control set to 6). After centrifugation at 45000 g for 45 min, the supernatant was discarded and the pellet containing gliadin protein was resuspended in 50 ml of 7 M urea in 50 mM Tris (pH=8.0). The suspension was again centrifuged at 45000 g for 45 min and the supernatant was harvested for purification. The supernatant containing α2-gliadin was incubated with 1 ml of nickel-nitrilotriacetic acid resin (Ni-NTA; Qiagen) overnight and then batch-loaded on a column with 2 ml of Ni-NTA. The column was washed with 7M urea in 50 mM Tris (pH=8.0), and α2-gliadin was eluted with 200 mM imidazole, 7 M urea in 50 mM Tris (pH=4.5). The fractions containing α2-gliadin were pooled into a final concentration of 70% ethanol solution and two volumes of 1.5M NaCl were added to precipitate the protein. The solution was incubated at 4° C. overnight and the final precipitate was collected by centrifugation at 45000 g for 30 min, rinsed in water, and re-centrifuged to remove the urea. The final purification step of the α-2 gliadin was developed with reverse-phase HPLC. The Ni-NTA purified protein fractions were pooled in 7 M urea buffer and injected to a Vydac (Hesperia, Calif.) polystyrene reverse-phase column (i.d. 4.6 mm×25 cm) with the starting solvent (30% of solvent B:1:1 HPLC-grade acetonitrile/isopropanol:0.1% TFA). Solvent A was an aqueous solution with 0.1% TFA. The separation gradient extended from 30-100% of solvent B over 120 min at a flow rate of 0.8 ml/min.

TABLE 2

Amount of Peptides Digested after 15 hours

| | 33-mer | Control A | Control B |
|---|---|---|---|
| H1P0 | <20% | >90% | >90% |
| H2P0 | <20% | >61% | >85% |
| H3P0 | <20% | >87% | >95% |
| H4P0 | <20% | >96% | >95% |
| H5P0 | <20% | >96% | >95% |

The purity of the recombinant gliadin was >95%, which allowed for facile identification and assignment of proteolytic products by LC-MS/MS/UV. Although many previous studies utilized pepsin/trypsin treated gliadins, it was found that, among gastric and pancreatic proteases, chymotrypsin played a major role in the breakdown of α2-gliadin, resulting in many small peptides from the C-terminal half of the protein and a few longer (>8 residues) peptides from the N-terminal half, the most noteworthy being a relatively large fragment, the 33-mer (SEQ ID NO:12) LQLQPF-PQPQLPYPQPQLPYPQPQLPYPQPQPF (residues 57-89). This peptide was of particular interest for two reasons: (a) whereas most other relatively stable proteolytic fragments were cleaved to smaller fragments when the reaction times were extended, the 33-mer peptide remained intact despite prolonged exposure to proteases; and (b) three distinct patient-specific T cell epitopes identified previously are present in this peptide, namely, (SEQ ID NO:20) PFPQPQLPY, (SEQ ID NO:21) PQPQLPYPQ (3 copies), and (SEQ ID NO:22) PYPQPQLPY (2 copies).

Figure 4:
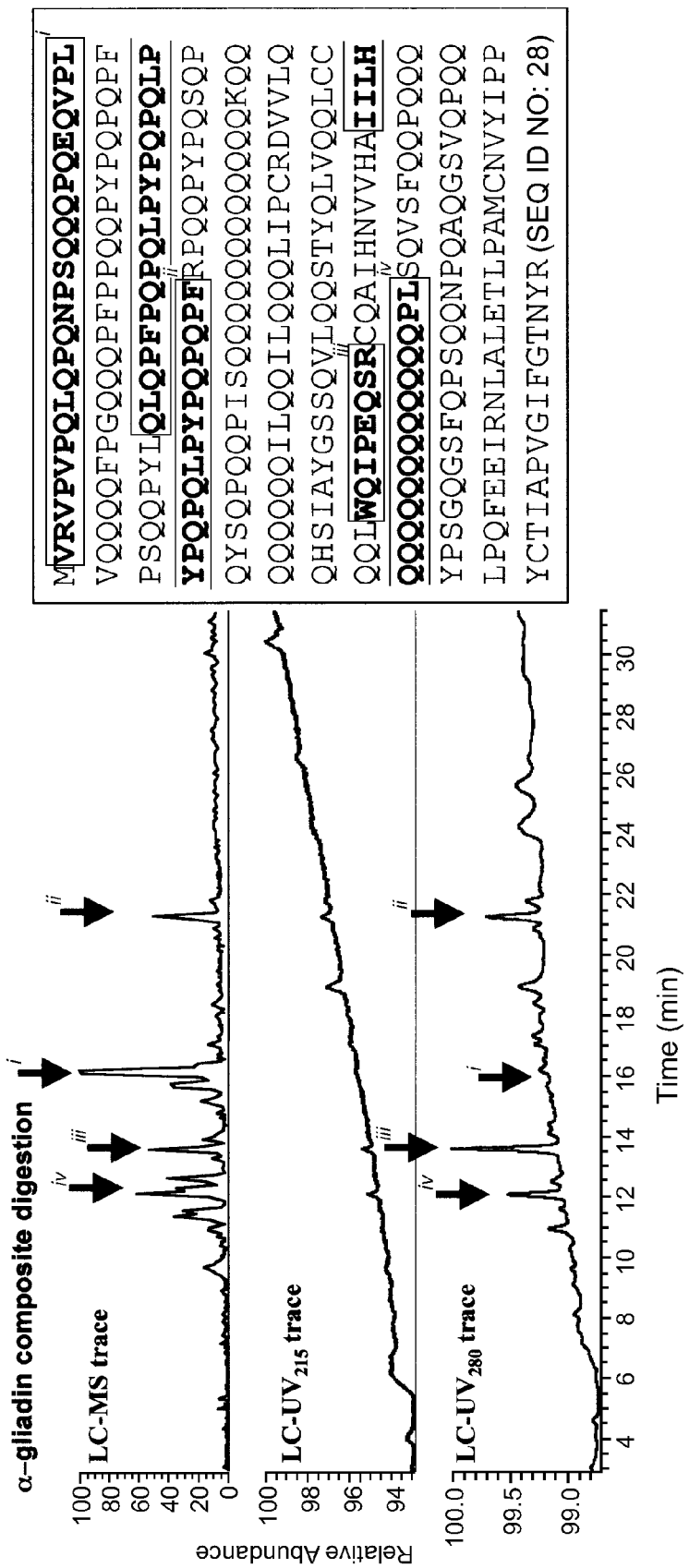
FIG. 4. Products of gastric and pancreatic protease mediated digestion of 2-gliadin under physiological conditions. Analysis was performed by LC-MS. The longest peptides are highlighted by arrows and also in the sequence of 2-gliadin (inset).

To establish the physiological relevance of this peptide, composite gastric/pancreatic enzymatic digestion of α2 gliadin was then examined. As expected, enzymatic digestion with pepsin (1:100 w/w ratio), trypsin (1:100), chymotrypsin (1:100), elastase (1:500) and carboxypeptidase (1:100) was quite efficient, leaving behind only a few peptides longer than 9 residues (the minimum size for a peptide to show class II MHC mediated antigenicity) (FIG. 4). In addition to the above-mentioned 33-mer, the peptide (SEQ ID NO:23) WQIPEQSR was also identified, and was used as a control in many of the following studies. The stability of the 33-mer peptide can also be appreciated when comparing the results of a similar experiment using myoglobin (another common dietary protein). Under similar proteolytic conditions, myoglobin is rapidly broken down into much smaller products. No long intermediate is observed to accumulate.

The small intestinal brush-border membrane (BBM) enzymes are known to be vital for breaking down any remaining peptides from gastric/pancreatic digestion into amino acids, dipeptides or tripeptides for nutritional uptake. Therefore a comprehensive analysis of gliadin metabolism also required investigations into BBM processing of gliadin peptides of reasonable length derived from gastric and pancreatic protease treatment. BBM fractions were prepared from rat small intestinal mucosa. The specific activities of known BBM peptidases were verified to be within the previously reported range. Whereas the half-life of disappearance of WQIPEQSR was ~60 min. in the presence of 12 ng/µl BBM protein, the half-life of (SEQ ID NO:12) LQLQPF-PQPQLPYPQPQLPYPQPQLPYPQPQPF digestion was >20 h. Therefore, the latter peptide remains intact throughout the digestive process in the stomach and upper small intestine, and is poised to act as a potential antigen for T cell proliferation and intestinal toxicity in genetically susceptible individuals.

Verification of proteolytic resistance of the 33-mer gliadin peptide with brush border membrane preparations from human intestinal biopsies: to validate the conclusions reached as described in Example 1, which describes studies with rat BBM preparations, in the context of human intestinal digestion, BBM preparations were prepared from a panel of adult human volunteers, one of whom was a Celiac Sprue patient in remission, while the rest were found to have normal intestinal histology. (SEQ ID NO:12) LQLQPF-PQPQLPYPQPQLPYPQPQLPYPQPQPF, (SEQ ID NO:1) QLQPFPQPQLPY (an internal sequence from the 33-mer used as a control), WQIPEQSR and other control peptides (100 µM) were incubated with BBM prepared from each human biopsy (final aminopeptidase N activity of 13 µU/µl) at 37° C. for varying time periods. While (SEQ ID NO:1) QLQPFPQPQLPY, (SEQ ID NO:23) WQIPEQSR and other control peptides were completely proteolyzed within 1-5 h, the long peptide remained largely intact for at 19 hours. These results confirm the equivalence between the rat and human BBM for the purpose of this study. Moreover, these results indicate that the methods, foodstuffs, and other reagents of the invention can be used in humans not known to have Celiac Sprue to improve digestion and reduce any ill effects of the long peptide.

Figure 5:
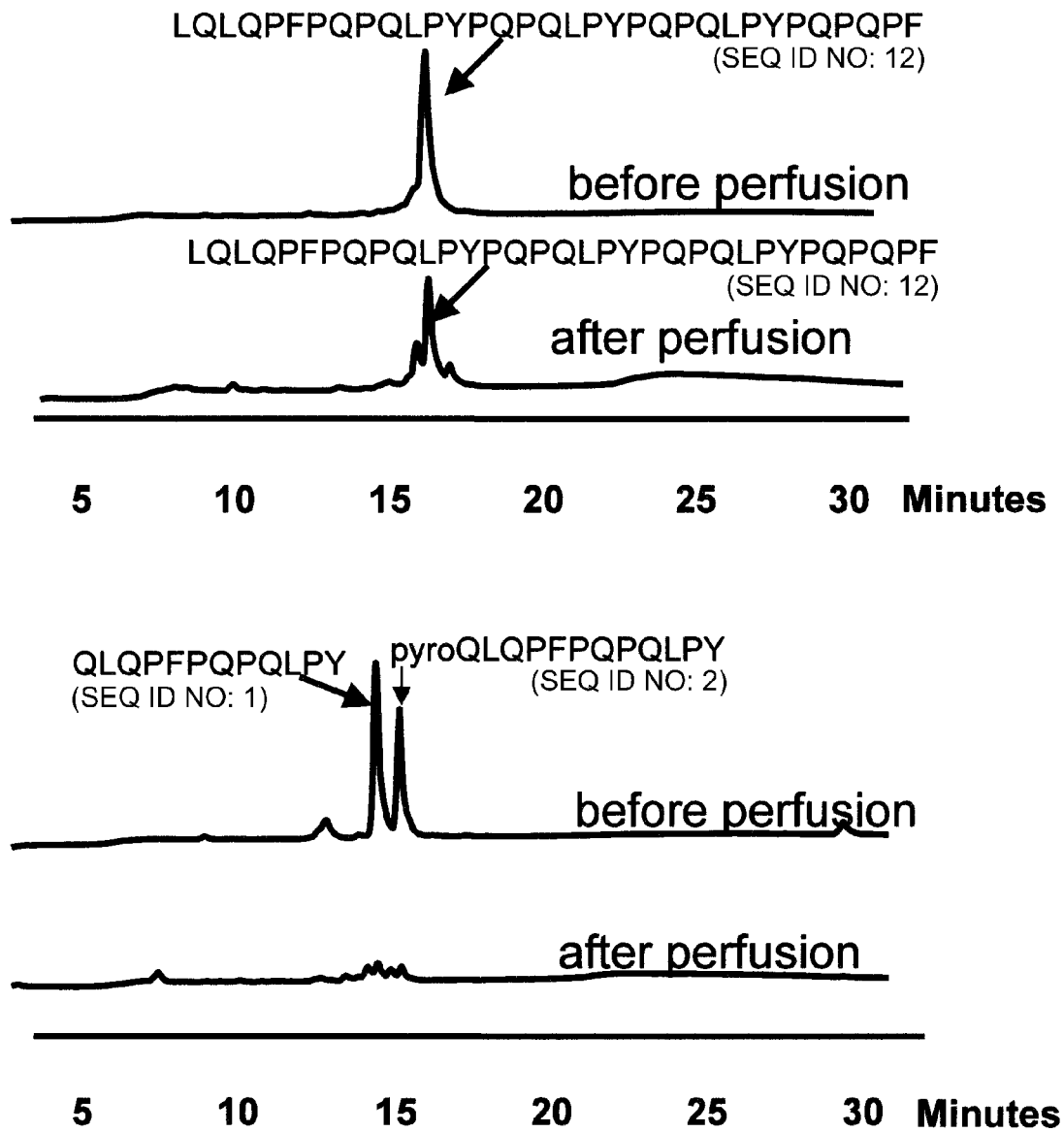
FIG. 5. In vivo brush border membrane digestion of peptides. LC-UV215 traces of 25 M of (SEQ ID NO:12) LQLQPFPQPQLPYPQPQLPYPQPQLPYPQPQPF before perfusion and after perfusion (residence time=20 min). LC-UV215 traces of 50 M of SEQ ID NO:1 QLQPFPQPQLPY before perfusion and after perfusion (residence time=20 min).

Verification of proteolytic resistance of the 33-mer gliadin peptide in intact animals: The proteolytic resistance of the 33-mer gliadin peptide, observed in vitro using BBM from rats and humans, was confirmed in vivo using a perfusion protocol in intact adult rats (Smithson and Gray (1977) *J. Clin. Invest.* 60:665). Purified peptide solutions were perfused through a 15-20 cm segment of jejunum in a sedated rat with a residence time of 20 min, and the products were collected and subjected to LC-MS analysis. Whereas >90% of (SEQ ID NO:1) QLQPFPQPQLPY was proteolyzed in the perfusion experiment, most of the 33-mer gliadin peptide remained intact. These results demonstrate that the 33-mer peptide is very stable as it is transported through the mammalian upper small intestine. The data is shown in FIG. 5.

The 33-mer gliadin peptide is an excellent substrate for tTGase, and the resulting product is a highly potent activator of patient-derived T cells: studies have demonstrated that regiospecific deamidation of immunogenic gliadin peptides by tTGase increases their affinity for HLA-DQ2 as well as the potency with which they activate patient-derived gluten-specific T cells. It has been shown that the specificity of tTGase for certain short antigenic peptides derived from gliadin is higher than its specificity toward its physiological target site in fibronectin; for example, the specificity of tTGase for the α-gliadin derived peptide (SEQ ID NO:3) PQPQLPYPQPQLPY is 5-fold higher than that for its target peptide sequence in fibrinogen, its natural substrate. The kinetics and regiospecificity of deamidation of the 33-mer α-gliadin peptide identified as above were therefore measured. The $k_{cat}/K_M$ was higher than that reported for any peptide studied thus far: kcat/KM=440 min-1 mM-1 for (SEQ ID NO:12) LQLQPF-PQPQLPYPQPQLPYPQPQLPYPQPQPF compared to kcat/KM=82 min-1 mM-1 for PQPQLPY and kcat/KM=350 min-1 mM-1 for (SEQ ID NO:3) PQPQLPYPQPQLPY.

Moreover, LC-MS-MS analysis revealed that the peptide (SEQ ID NO:12) LQLQPF-PQPQLPYPQPQLPYPQPQLPYPQPQPF was selectively deamidated by tTGase at the underlined residues. Because tTGase activity is associated with the brush border membrane of intestinal enterocytes, it is likely that dietary uptake of even small quantities of wheat gluten will lead to the build-up of sufficient quantities of this 33-mer gliadin peptide in the intestinal lumen so as to be recognized and processed by tTGase.

Figure 6:
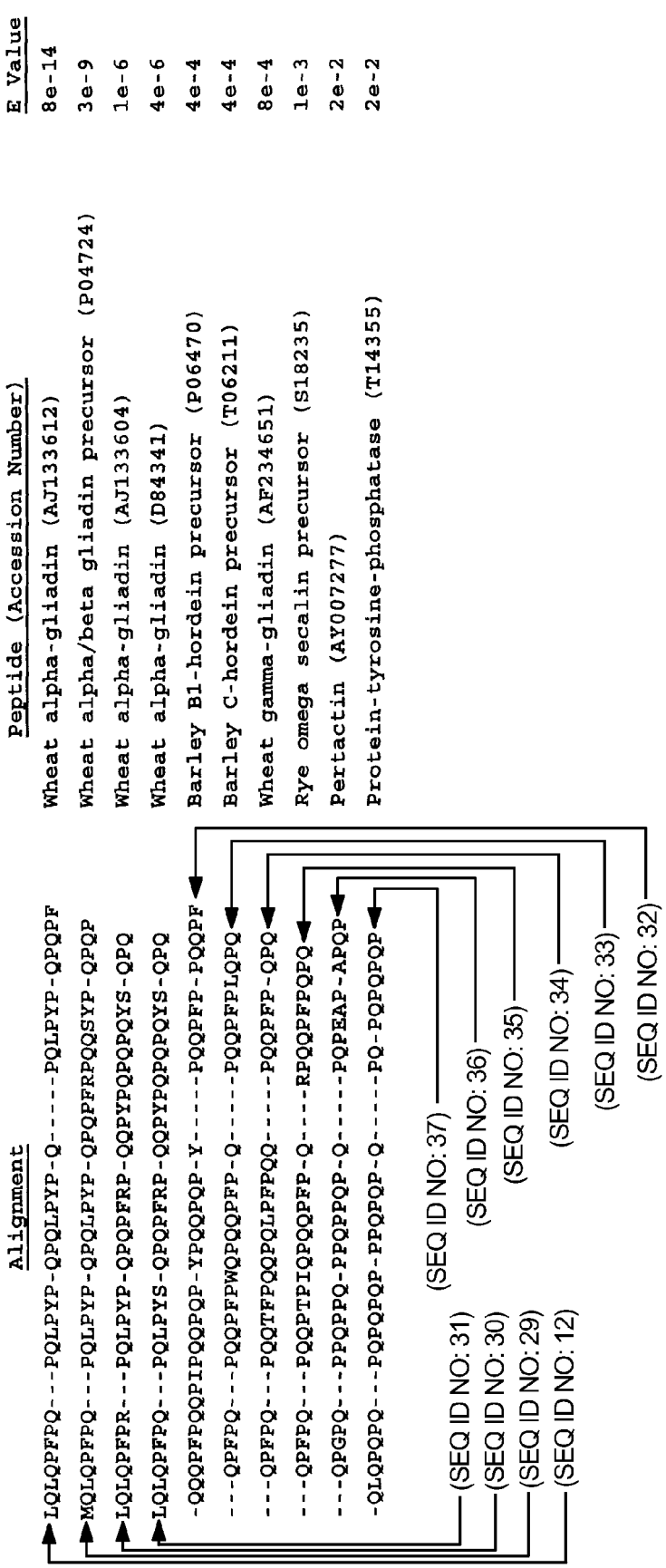
FIG. 6. Alignment of representative gluten and non-gluten peptides homologous to (SEQ ID NO:12) LQLQPFPQPQLPYPQPQLPYPQPQLPYPQPQPF.

Structural characteristics of the 33-mer gliadin peptide and its naturally occurring homologs: Sequence alignment searches using BLASTP in all non-redundant protein databases revealed several homologs (E-value<0.001) of the 33-mer gliadin peptide, shown in FIG. 6. Interestingly, foodgrain derived homologs were only found in gliadins (from wheat), hordeins (from barley) and secalins (from rye), all of which have been proven to be toxic to Celiac Sprue patients. Nontoxic foodgrain proteins, such as avenins (in oats), rice and maize, do not contain homologous sequences to the 33-mer gliadin. In contrast, a BLASTP search with the entire α2-gliadin sequence identified foodgrain protein homologs from both toxic and nontoxic proteins. Based on available information regarding the substrate specificities of gastric, pancreatic and BBM proteases and peptidases, it is believed that, although most gluten homologs to the 33-mer gliadin peptide contained multiple proteolytic sites and are therefore unlikely to be completely stable toward digestion, several sequences from wheat, rye and barley are expected to be resistant to gastric and intestinal proteolysis. The stable peptide homologs to the 33-mer α2-gliadin peptide are (SEQ ID NO:24) QPQPFPPQLPYPQTQPFP-PQQPYPQPQPQYPQPQ (from α1- and α6-gliadins); (SEQ ID NO:25) QQQPF-PQQPIPQQPQPYPQQPQPYPQQPFPPQQPF (from B1 hordein); (SEQ ID NO:26) QPFPQPQQTFPQQPQLPF-PQQPQQPFPQPQ (from γ-gliadin); (SEQ ID NO:27) QPF-PQPQQPTPIQPQQPFPQRPQQPFPQPQ (from ω-secalin). These stable peptides are all located at the N-terminal region of the corresponding proteins. The presence of proline residues after otherwise cleavable residues in these peptides would contribute to their proteolytic stability.

Figure 7:
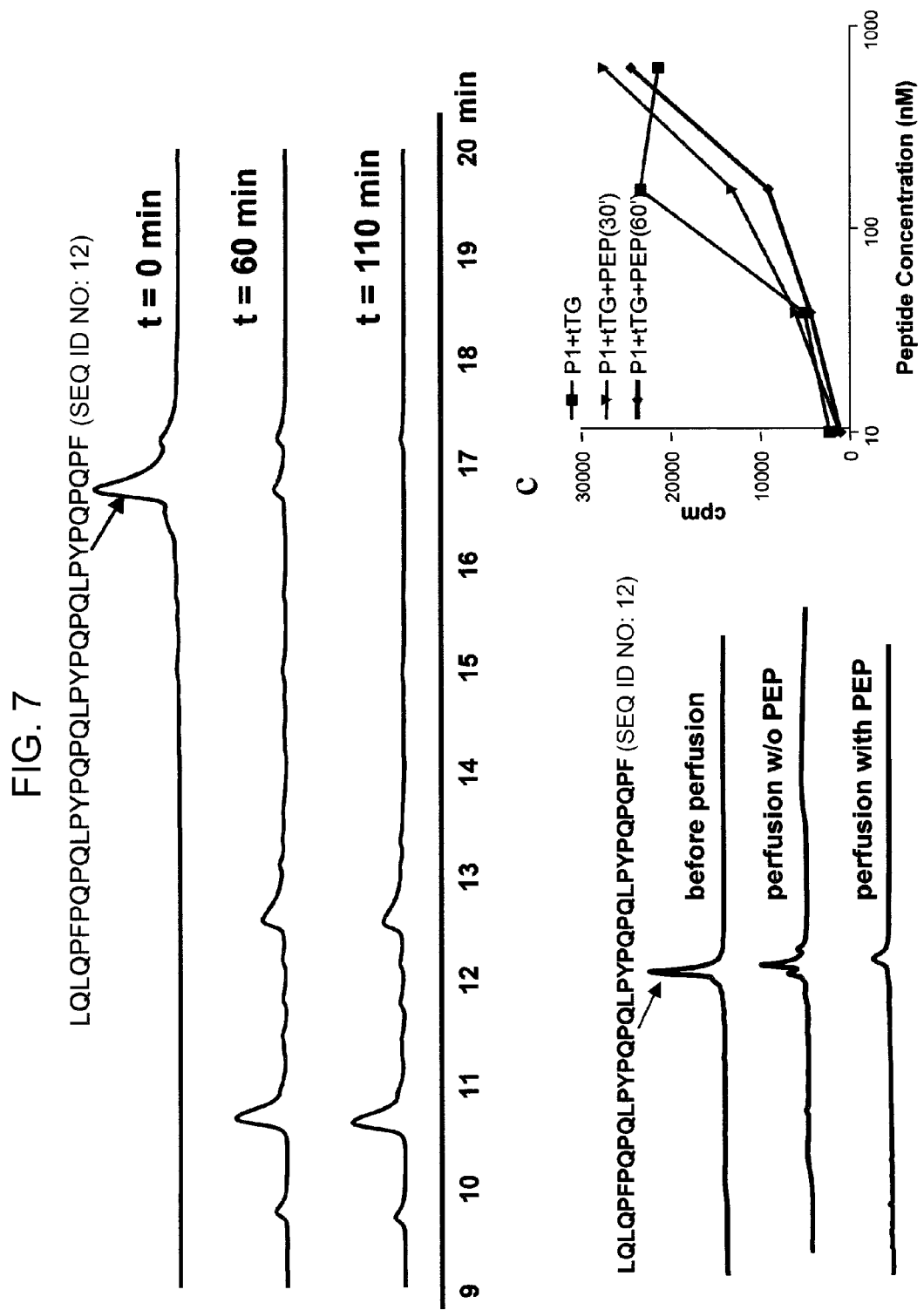
FIG. 7. Breakdown and detoxification of 33-mer gliadin peptide with PEP. In vitro incubation of PEP (540 mU/ml) with the 33-mer gliadin peptide (100 M) for the indicated time. In vivo digestion of the 33-mer gliadin peptide (25 M) with PEP (25 mU/ml) and the rat's intestine (residence time=20 min).

Bacterial Prolyl Endopeptidase Rapidly Detoxifies the 33-Mer Gliadin Peptide:

The abundance and location of proline residues is a crucial factor contributing to the resistance the 33-mer gliadin peptide toward gastrointestinal breakdown. In accordance with the methods of the invention, a prolyl endopeptidase can catalyze breakdown of this peptide, thereby diminishing its toxic effects. Preliminary in vitro studies with short gliadin peptides and the prolyl endopeptidase (PEP) from *F. meningosepticum* demonstrate this aspect of the invention. The ability of this PEP to clear the 33-mer gliadin peptide was evaluated via in vitro and in vivo experiments. Using both rat BBM and co-perfusion of the peptide and PEP in intact rat intestines, this detoxification was demonstrated. The results are shown in FIG. 7. Together these results highlight the potential of detoxifying gluten in Celiac Sprue patients by peptidase therapy.

Although gluten proteins from foodgrains such as wheat, rye and barley are central components of a nutritious diet, they can be extremely toxic for patients suffering from Celiac Sprue. To elucidate the structural basis of gluten toxicity in Celiac Sprue, comprehensive proteolytic analysis was performed on a representative recombinant gliadin under physiologically relevant conditions. An unusually long and proteolytically stable peptide product was discovered, whose physiological relevance was confirmed by studies involving brush border membrane proteins from rat and human intestines as well as intestinal perfusion assays in live rats. In aggregate, these data demonstrate that this peptide and its homologs found in other wheat, rye and barley proteins contribute significantly to the inflammatory response to dietary wheat in Celiac Sprue patients.

The absence of satisfactory animal models for Celiac Sprue implies that the pivotal pathogenic nature of the gluten peptides identified in this study can only be verified in human patients. While this is likely to be a formidable task, and would in any event need to be conducted in a manner that would not harm the patient, the results above demonstrate that the deleterious effects of gluten ingestion by Celiac Sprue patients can be ameliorated by enzyme treatment of gluten containing foods. Specifically, co-administration of a bioavailable form of a suitable prolyl endopeptidase with dietary gluten would attenuate its toxicity by cleaving the stable 33-mer peptide into non-immunogenic products. Given the absence of a satisfactory therapeutic option for Celiac Sprue and the notorious difficulty associated with long-term maintenance of a gluten-free diet, the peptidase therapies of the present invention provides an alternative to strict abstinence for the rapidly growing numbers of individuals affected by this disease.

Example 3

Peptidase Supplementation as Therapy for Celiac Sprue

Demonstration of Efficacy and Safety in Rats and Humans In Vivo

As described above, Celiac Sprue is a disease engendered by the gliadin peptides in wheat, rye, or barley that interact with the small intestine to produce a cascade of events leading to the destruction of intestinal mucosa and consequent malabsorption of nutrients and vitamins. Gliadin peptides are highly resistant to digestion by gastric, and pancreatic proteases as well as by the integral peptidases of the intestinal brush border surface. The interaction of recombinant α-gliadin with mammalian pepsin, chymotrypsin, trypsin, and elastase has shown that a 33-residue peptide rich in glutamine (Q) and proline(P) residues ((SEQ ID NO:12) LQLQPF-PQPQLPYPQPQLPYPQPQLPYPQPQPF) is a major final digestion product. When this 33-mer is exposed to intact rat small intestine or to human intestinal brush border membranes, it is impervious to additional breakdown. This peptide has very high specificity for stimulating T cell proliferation in peripheral blood lymphocyte cultures from Celiac Sprue patients but not in lymphocyte cultures from normal individuals. Because of the resistance of this and other gliadin peptides to pancreatic and intestinal digestion and the abundance of proline residues in these peptides, the 33-mer and other gliadin peptides were exposed to a prolyl endopeptidase, which demonstrated that this enzyme is highly effective under physiologic conditions in breaking the peptide bonds between the proline and the next residue on the peptide chain. The consequent cleavage of the gliadin peptide rendered it incapable of inducing lymphocyte proliferation, demonstrating that the additional processing of the gliadin peptide should prevent its toxic reaction to the intestine in Celiac Sprue patients.

This example describes experiments to demonstrate that a PEP is effective in further digesting the toxic gliadin peptides under physiological conditions. Celiac Sprue patients, in accordance with the methods of the present invention, can consume a normal diet along with a PEP supplement that will digest the toxic gliadin peptide and circumvent the reaction that leads to T-cell proliferation and destruction of the intestinal mucosa. This is an alternative and innovative treatment in Celiac Sprue—the substitution of a rigid gluten-free diet with an exogenous digestive endopeptidase that promotes metabolism and essential detoxification of the gliadin peptide. The studies described in this Example can be used to document efficacy and safety and include a pilot study in controls and Celiac patients with PEP-treated wheat flour. These are important studies that enable the institution of a full clinical trial in normal humans and those with Celiac Sprue.

The studies described in this example include the following:
1. To determine whether exogenous peptidase supplementation digests resistant gliadin peptides to non-toxic, absorbable products in the rat in vivo under physiologic conditions. This study involves:
A. Expression and purification of recombinant Prolyl Endopeptidase (rPEP);
B. Examination of rPEP action on gliadin peptides in rat intestine in vivo; and determination of optimal conditions for efficient digestion and analysis of effects on intestinal structure and function with acute and chronic administration.
2. To perform preliminary clinical testing of the efficacy of PEP in processing the resistant gliadin peptides in wheat flour to non-toxic products.
3. To establish the ideal conditions for packaging the rPEP to achieve efficient digestion of gliadin peptides in vivo, including the preparation of formulations of rPEP (polyanhyride capsules, methacrylate-glycol capsules; OROS).

As described in the preceding examples, experiments involving exposure of α-gliadin to purified pancreatic proteases have demonstrated the production of a 33-residue glutamine and proline-rich peptide ((SEQ ID NO:12) LQLQPFPQPQLPYPQPQLPYPQPQLPYPQPQPF) as a major end product. When this peptide is administered by perfusion into the small intestine of the intact rat under physiologic conditions or incubated with human intestinal brush border membranes, its digestion is relatively retarded as compared to that for most dietary peptides such as myoglobin from peripheral muscle. Experiments demonstrate that a prolyl endopeptidase (PEP) (from *Flavobacterium meningosepticum*) at molar concentrations only one one-hundredth of those of the digestive resistant 33-mer gliadin peptide is capable of efficiently cleaving it to smaller peptides that are 1) non-toxic residual peptides (as estimated from the human T cell proliferation assay), and 2) can be readily further digested and absorbed by the rat intestine. The conditions for optimal action of the PEP on the resistant α-gliadin 33-mer peptide and other gliadin peptides that react in the T cell proliferation assay can be determined by the methods set forth in this example.

To demonstrate that exogenous peptidase supplementation digests resistant gliadin peptides to non-toxic, absorbable products in vivo under physiologic conditions, expression and purification of recombinant Prolyl Endopeptidase (rPEP) can be undertaken. Recombinant prolyl endopeptidase (rPEP) from *Flavobacterium meningosepticum* can be constructed and expressed as detailed by Yoshimoto Tet al., and by Uchiyama et al. One can also obtain recombinant preparations of a PEP enzyme from *Aeromonas Hydrophila* as detailed by Shen et al. or from *Sphingomonas capsulate* (Kabashima T, Fujii M, Meng Y, Ito K, Yoshimoto T., Prolyl endopeptidase from *Sphingomonas capsulate*: isolation and characterization of the enzyme and nucleotide sequence of the gene, Arch Biochem Biophys. 1998 Oct 1; 358(1):141-8.)

To demonstrate rPEP action on gliadin peptides in rat intestine in vivo and to determine optimal conditions for efficient digestion, intestinal perfusion studies in intact rats can be performed as follows. Sprague-Dawley rats (300-400 gms) are anesthetized with pentobarbital, the abdomen entered through a midline incision, and a 10-20-cm length of jejunum isolated and catheterized as detailed previously. A test peptide (1 mM GLGG) known to be digested efficiently at the intestinal surface is perfused through the isolated segment at 0.4 ml per min in 154 mM NaCl/0.1% polyethylene glycol to allow calculation for any water flux. The disappearance of the test peptide and the appearance of any products will allow calculation of the intestinal surface digestion and absorption. These results are compared with those with the digestive resistant gliadin peptides (SEQ ID NO:1) QLQPFPQPQLPY, (SEQ ID NO:3) PQPQLPYPQPQLPY, and the 33-mer (SEQ ID NO:12) LQLQPFPQPQLPYPQPQLPYPQPQLPYPQPQPF. The GLGG peptide is readily hydrolyzed to free Leu and Gly and to the dipeptide GG; the high proline content of the gliadin peptides makes them poor substrates for the available intestinal membrane peptidases. The intestinal luminal samples taken at the site of the distal catheter are analyzed by Liquid Chromatography-Mass Spectrometry (SpectraSystem, ThermoFinnigan) on a C18 reversed phase column, as previously detailed. Peptide fragments are detected and their identities confirmed by mass spectrometry fragmentation patterns under conditions where there is a linear relationship of these peptides and their products.

After the relative degree of digestion and absorption of the GLGG and gliadin peptides has been established, experiments to demonstrate the efficacy of PEP in digesting the peptides in this in vivo rat model can be performed. Initially, the PEP is perfused via a separate catheter at the proximal infusion site of the isolated jejunal segment at molar concentrations ranging from 1:1000 to 1:1 of that of the test peptides. Preliminary experiments show that a molar ratio of PEP: peptide of 1:100 is sufficient for efficient cleavage at the C-terminus of internal Prolyl residues to the gliadin sequence. But, it is also important to test the PEP at higher concentrations, in case more peptidase activity is required and desired for total cleavage of the gladin peptides and to assess side effects on the integrity of the intestine and other organs. After each experiment, the intestine and other abdominal organs (especially liver and kidney) are recovered, aliquots quick frozen and preserved at −70° for subsequent assay of intestinal carbohydrases (sucrase, lactase, maltase) and peptidases (aminopeptidase N, carboxypeptidase, dipeptidyl peptidase IV), and the tissues are fixed in formalin, stained for hematoxylin-eosin, and examined ("blindly" without knowledge of the experimental protocol) for any histological changes, with particular attention paid to any structural effects that might be produced of the higher PEP concentrations.

Once the ideal ratio of PEP to gliadin peptide is determined in these perfusion experiments, one can analyze the capacity of the PEP to enhance the hydrolysis of gluten peptides in commercial gluten-containing wheat flour. A 1% slurry of the flour mixed with 1:100 (weight basis) trypsin and chymotrypsin, and 1:500 (weight basis) elastase is perfused into the intestine with or without co-perfusion of suitable quantities of the PEP. LC-MS analysis of the residual gliadin products is conducted on the collected samples, and the histologic and enzymatic parameters are examined, as described above.

Feeding studies in intact rats can be conducted as follows. Once the ideal ratio of the PEP to the gliadin substrate has been established in the perfusion experiments, rats are fed 70% carbohydrate chow containing wheat flour, which is used as the conventional rat chow for periods of two weeks. Control rats are fed only the special chow, and the treated rats are given sufficient PEP supplementation (molar ratios PEP to gliadin protein: 1:1, 1:10 and 1:100) in the diet to digest the residual gliadin peptides such as the Pro- and Gln-rich 33-mer. After two weeks of ab lib feeding, the rats' daily consumption of food is quantified by daily weighing of the residual chow in the feeder and the nutritional assessment determined by daily body weights. Over the feeding period of 2-4 weeks, rats are weighed and examined daily to verify normal activities and are then killed by stunning and decapitation. The intestine, liver and kidneys are recovered and examined for gross and histological integrity, and any anatomic differences are noted between the control (PEP−) and treated (PEP+) animals. In addition, digestive enzymes (carbohydrases and proteases) are determined, as detailed for the rat perfusion studies.

Preliminary clinical testing of the efficacy of PEP in processing the resistant gliadin peptides can be conducted as follows. Now that it has been established that PEP can readily convert the high-Pro, high-Gln gliadin peptides to smaller, non-toxic fragments that do not produce proliferation in the T cell assay, preliminary testing of PEP treated wheat flour containing the usual or enhanced amounts of gluten (e.g., Bob's RedMill flour, Milwaukee, Oreg.) or food-grade gluten or gliadin itself (e.g. gliadin from Sigma Aldrich) can be undertaken. The flour, gluten or gliadin can be batch treated with appropriate amounts of purified mixtures of pancreatic enzymes that are used clinically to treat pancreatic insufficiency (e.g., Pancrease MT 20 containing 20,000 units lipase, 44000 units of the pancreatic proteases and 56000 units of amylase per capsule). Incubation of a slurry of flour, gluten or gliadin with the material from an appropriate amount of capsules of the Pancrease preparation can be carried out in 0.02 M Na—K phosphate buffer, pH 6.5 at 37° C. for several hours under sterile conditions until 1) standard T cell proliferation assays (see, for example, Arentz-Hansen, 2000) identifies the highly active signal produced by the gliadin peptides and particularly 33-mer, ((SEQ ID NO:12) LQLQPF-PQPQLPYPQPQLPYPQPQLPYPQPQPF) and 2) the average size of the proteolytically derived gliadin peptides has been reduced to <6 residues (as measured by gel filtration HPLC). The pre-digested flour, gluten or gliadin is then exposed to sufficient pure PEP (for example, 1 mole PEP:100 moles gliadin substrate) under sterile conditons for 1-18 hours, and the cleavage of gliadin peptides with known toxicity such as the 33-mer verified by LC-MS analysis. In parallel control studies, previously denatured PEP (by heating to 90° C. for 60 min) can be incubated with the protease-treated flour and the persistence of these toxic peptides is verified by LC-MS analysis. These tests demonstrate the usefulness of a the 33-mer in assays; in one aspect, the present invention provides the 33-mer in isolated and purified forms, as well as assays to detect its present in foodstuffs.

The pre-treated flours can be incorporated into otherwise gluten-free breakfast muffins by a nutritionist, and these served to volunteer persons and those with biopsy-proven Celiac Sprue at a "community" breakfast in the nutrition department for a period of two weeks. Patients must have uncomplicated Celiac Sprue that is in remission on gluten exclusion alone. Control volunteers who have been established not to have Celiac Sprue and negative Celiac antibody studies are also recruited. During this period the control muffins made with flour that has been treated with denatured pancreatic proteases±PEP are given. The PEP+ muffins are given for the first two weeks followed by a two week break from the breakfasts, and the PEP− muffins are administered over the second two week breakfast sessions. The study can be single-blinded, the subjects being unaware of whether PEP is included in the study. The physician and nutritionist will know the flour has been exposed only to the pancreatic proteases or also to PEP, in case there are any untoward reactions to the PEP material. All study subjects will fill out a questionnaire regarding their observations during each two week period as well as during the two week break time and the two weeks after the second muffin breakfast period. Although obtaining a biopsy via endoscopy would be an ideal monitor of the PEP efficacy, this cannot be ethically justified based on currently available data. Endoscopy may be offered only if needed as an aspect of patient care. Participants will initially meet briefly with the responsible physician-investigator who will be available throughout the study. Participants will be interviewed and the questionnaire reviewed by a nutritionist and physician before the study, at the end of each two week period and two weeks after completing the study. The principal investigator will be ultimately responsible for the conduct of the trial and will meet regularly with the responsible physician and nutritionist to whom the day to day aspects of the study will be delegated. Adults from age 17 and older can be eligible for the study. Both males and females with Celiac Sprue will be recruited through Celiac support organizations. Individuals from various ethnic groups, including Asian and African American can be recruited, although most patients with Celiac Sprue are Caucasians. Both males and females can participate; there is a somewhat higher proportion of female Celiac Sprue patients (~65%). Participants will have 24 hour access to the gastroenterology team, and a member of the research team will be available for consultation. Efficacy will be monitored by the comparative responses of participants during the control period when ingesting protease-treated flour without the PEP versus the same flour that has been treated with PEP.

Suitable conditions for packaging the rPEP to achieve efficient digestion of gliadin peptides in vivo can be determined as follows. To develop a palatable preparation of PEP to enable the in vivo digestion of the toxic peptides in humans, it can be useful to formulate PEP so that it can pass into the small intestine without being destroyed by the harsh acidic environment of the stomach. In addition, this formulation can provide rapid release of PEP upon entry into the duodenum, where the secreted pancreatic proteases exert their maximal action within the luminal contents to cleave dietary proteins. There are several well-studied and widely used examples of such delivery systems for other substances. The development of an optimized formulation for an effective PEP drug capable of delivering pharmacologically useful quantities of this enzyme into the upper small intestine as a digestive supplement can be conducted as follows. To process the digestive-resistant gliadin peptides, selected formulation strategies that have been used successfully for the delivery of other enzyme supplements can be used. In particular, previously used formulations for pancreatic proteases and lactase are evaluated by use of recombinant PEP from *Flavobacterium meningoscepticum* and *Aeromonas hydrophila*. These enzymes are expressed and purified as described by A. Kitazono et al. and A. Kanatani et al. Pancreatic enzymes have been used for the past seventy years to treat pancreatic exocrine insufficiency. Although early clinical results were variable due to gastric inactivation of the exogenously administered enzymes, a revived interest in enzyme-containing digestive aids occurred around 1960 with the development of acid stable enteric coatings (I. R. Wilding, S. S. Davis, and D. T. O'Hagan, Targeting of drugs and vaccines to the gut. *Pharmac. Ther.* 62, 97-124, (1994)). Similarly, acid stable enteric coatings have also been used for the delivery of lactase into the duodenum of patients with lactase deficiency. In one embodiment, the glutenase formulations of the invention comprise a glutenase in a stable enteric coating.

Lyophilized, particulate PEP mixed with bicarbonate (as buffer) is coated with Eudragit S100, L30D or L 100-44 according to manufacturer's instructions (Rohm America). Alternatively, cellulose acetate phthalate, methylcellulose or hydroxypropylmethyl cellulose phthalate can be used as coatings for the preparation of gastric acid resistant pellets. These enteric coatings are commonly used for the formulation of pancreatin (see T. Sipos (1978), Preparation of enteric coated digestive enzyme compositions, U.S. Pat. No. 4,079,125; and T. Sipos (1998), High buffer-containing enteric coating digestive enzyme bile acid compositions and method of treating digestive disorders therewith, U.S. Pat. No. 5,750,104).

An alternative strategy useful in preparing formulations of the invention, used successfully with lactase (B. J. Langner (1999), Enteric polymer coated capsule containing dried bacterial culture for supplying lactase, U.S. Pat. No. 6,008,027), involves filling gelatin capsules with 50-90% lyophilized PEP, the remaining capacity being filled with stabilizing dessicants such as silicon oxide, silicon dioxide or microcrystalline cellulose and bicarbonate buffer. The capsules are enterically coated with Eudragit polymer (Rohm America) or polyvinyl acetate phthalate (Sureteric, Merck Frosst) and vacuum dried prior to use. Similarly, diastase has been formulated with Eudragits RS100 and cellulase acetate phthalate coatings for enteric use (S. P. Vyas, P. J. Gogoi, S. Pande, and V. K. Dixit, Enteric spherules diastase in enzyme preparations. *J. Microencapsulation.* 8, 447-454, 1991). To demonstrate that these or other formulations increase PEP bioavailability in the small intestine, one can perform the following experiments. First, the ability of PEP activity to withstand 0.5-2 h of simulated gastric treatment (pepsin, in 0.1N HCl, pH 2) can be evaluated. If >10% activity can be reproducibly retained, the formulation is exposed to simulated conditions in the duodenum (pH 6.5 buffer containing trypsin, chymotrypsin and carboxypeptidase at a 1:100 molar ratio and elastase at a 1:500 ratio to the putative α2-gliadin). Ideally, full release of PEP activity would be achieved within 15 minutes. Formulations that satisfy the above criteria are fed initially to adult rats in conjunction with gluten-free meals spiked with recombinant α2-gliadin (whose proteolytic behavior in response to gastric and pancreatic enzymes+PEP has been well characterized). PEP doses in the range of 10-1000 units/kg body weight can be evaluated. Animals are sacrificed two hours after meals, and the small intestinal derived contents are analyzed by LC-MS for residual PEP activity and the extent to which gliadin has been proteolyzed. In particular, the concentration of the 33-mer digestive-resistant gliadin peptide is estimated. Formulations that yield >90% reduction in concentration of this peptide are evaluated more extensively for potential toxicity, as detailed above for the initial rat studies with water soluble PEP.

The procedures described herein are performed under an approved Animal Protocol described below. Male Sprague-Dawley rats, 250-300 g, (or Fisher rats for studies of DPP IV deficient intestine) are allowed access to regular wheat-based rat chow until the experiment. Rats are allowed water only for 8 hours prior to the experiment to insure clearance of residual chow in the upper small intestine. After the rat is anesthetized with an intraperitoneal injection of pentobarbital (50 mg/Kg), the abdominal cavity is opened and a small incision made in a segment of jejunum located 10 cm beyond the ligament of Trietz. Cannulation is made with a polyethylene catheter (3 mm ID, 4 mm OD) and sutured 2 cm distal to the incision. A second cannula is placed in similar fashion 10 cm distal to the first with the cannula facing proximally. After rinsing the isolated, intact jejunal segment with Ringers solution (140 mM NaCl, 10 mM KHCO$_3$, 1.2 mM K$_2$HPO$_4$, 1.2 mM CaCl$_2$, 1.2 mM MgCl$_2$) at 37° C. to remove any intraluminal debris, the isolated loop of intestine is returned to the abdominal cavity. The incision is covered with clear plastic wrap, and intra-abdominal temperature maintained at 37° C. by positioning a 30 watt incandescent lap at ~30 cm from the animal. A 2 mM solution of a gliadin peptide of 7-14 residues (purified and characterized by HPLC-Mass Spectrometry) is perfused in Ringer's solution containing [$^{14}$C]inulin (a dilution-concentration marker) to establish a steady state of concentrations of residual peptide and smaller products at the collection distal collection site (previous studies with other peptides and carbohydrates have revealed the steady state to be achieved in 10-20 minutes). Samples collected at the distal site are recovered and analyzed by HPLC-MS for residual peptide and smaller peptide or amino acid products. Samples are collected over 3 successive 10 minute periods after a steady state is achieved, and a series of gliadin and non-gliadin peptides are used. Animals can usually be maintained under anesthesia for a period of 3 to 6 hours by the addition of small increments of pentobarbital (~5 mg per 30-60 minutes). At the end of the experiment, the intestinal segment and an adjacent control segment are recovered and samples taken from liver, kidney and blood for analysis of the test peptide and its products. Terminal euthanasia is accomplished by an overdose of anesthesia to produce apnea until there is no heart contraction.

While other methods and reagents can be employed for purposes of the present invention, this example provides enzymes, enzyme formulations, and animal and clinical testing protocols to demonstrate the efficacy of enzyme-mediated therapy for Celiac Sprue.

Example 4

Heterologous Expression of PEP in *Lactobacilli*

In one embodiment of the present invention, a Celiac Sprue patient is provided with a recombinant organism modified to express a PEP of the invention. The recombinant organism is selected from those organisms that can colonize the intestinal mucosa without detriment to the patient, thereby providing an endogenous source of PEP to the patient. As one example, *Lactobacilli* such as *L. casei* and *L. plantarium* can colonize the intestinal mucosa and secrete PEP enzymes locally. Given their widespread use in food processing, they can also be used as an efficient source of PEP for industrial (to treat foodstuffs) and medical (to prepare PEP for pharmaceutical formulation) use. PEPs can be expressed in such *lactobacilli* using standard recombinant DNA technologies. For example, Shaw et al. (Shaw, D M, Gaerthe, B; Leer, R J, Van der Stap, J G M M, Smittenaar, C.; Den Bak-Glashouwer, Heijne, M J, Thole, J E R, Tielen F J, Pouwels, P H, Havenith, C E G (2000) Immunology 100, 510-518) have engineered *Lactobacilli* species to express intracellular and surface-bound tetanus toxin. The intact PEP genes (including leader sequences for efficient bacterial secretion) can be cloned into shuttle expression vectors such as pLP401 or pLP503 under control of the (regulatable) amylase promoter or (constitutive) lactate dehydrogenase promoter, respectively. Alternatively, recombinant food grade *Lactobacilli* strains can be generated by site specific recombination technology (e.g. see. Martin M C, Alonso, J C, Suarez J E, and Alvarez M A Appl. Env. Microbiol. 66, 2599-2604, 2000). Standard cultivation conditions are used for *Lactobacilli* fermentation, such as those described by Martin et al.

Example 5

Heterologous Expression of PEP in Yeasts

Both naturally occurring and recombinant cells and organisms can be used to produce the glutenases useful in practice of the present invention. Preferred glutenases and producing cells include those from organisms known to be Generally Regarded as Safe, such as *Flavobacterium, Aeromonas, Sphingomonas, Lactobacillus, Aspergillus, Xanthomonas, Pyrococcus, Bacillus* and *Streptomyces*. Extracellular glutenase enzymes may be obtained from microorganisms such as *Aspergillus oryzae* and *Lactobacillus casei*. Preferred cells include those that are already used in the preparation of foodstuffs but have been modified to express a glutenase useful in the practice of the present invention. As one example, yeast strains such as *Saccharomyces cerevisiae* are useful for high level expression of secreted heterologous proteins. Genes encoding any of the PEPs described above (mature protein only) can be cloned in expression plasmids designed for optimal production of secreted proteins. An example of such a heterologous expression strategy is described in Parekh, R. N. and Wittrup, K. D. (Biotechnol. Prog. 13, 117-122, 1997). Either self-replicating (e.g. 2 micron) or integrating (e.g. pAUR101) vectors can be used. The GAL1-10 promoter is an example of an inducible promoter, whereas the ADH2 promoter is an example of a constitutive promoter. The cDNA encoding the mature PEP is fused downstream of a leader sequence containing a synthetic pre-pro region that includes a signal cleavage site and a Kex2p cleavage site. *S. cerevisiae* BJ5464 can be used as a host for production of the peptidase. Shake-flask fermentation conditions are described by Parekh and Wittrup in the above-cited reference. Alternatively, high cell density fed-batch cultures can be used for large scale production of the peptidases; a representative procedure for this purpose is described in Calado, C. R. C, Mannesse, M., Egmond, M., Cabral, J. M. S, and Fonseca, L. P. (Biotechnol. Bioeng. 78, 692-698, 2002).

Example 6

Enteric Capsule Formulation of Prolyl Endopeptidase

Gelatin capsules are filled with 100 mg prolyl endopeptidase and 10 mg of silicon dioxide. The capsules are enterically coated with Eudragit polymer and put in a vacuum chamber for 72 hours. The capsules are then held at a range of temperature of 10° C. to 37° C. and a controlled humidity level of 35-40%.

Example 7

Studies of Enteric Capsule Formulation of Prolyl Endopeptidase

A study is conducted where patients with Celiac Sprue are enrolled in a two week-long study. Gelatin capsules containing 90% prolyl endopeptidase mixed with 10% silicon dioxide are used. The capsules are hand-filled with the mixture, banded, and coated with a 10% Sureteric enteric coating (a polymer of polyvinylacetatephthalate developed by the Canadian subsidiary of Merck & Company). Samples are acid-tested by exposing the coating to 1N HCL for one hour in order to simulate the acid environment of the stomach. The capsules are then put in a vacuum chamber for 72 hours. Two 100 mg capsules are administered to each patient prior to each meal. The patients are instructed to eat all kinds of food without abstaining from those that were known to cause distress, e.g., bloating, diarrhea, and cramps.

Example 8

Enteric Pill Formulation of Prolyl Endopeptidase 400 mg of L-tartaric acid and 40 mg of polyethylene glycol-hydrogenated castor oil (HCO-60) are dissolved in 5 ml of methanol. This solution is placed in a mortar previously warmed to 30° C. To the solution is added 100 mg of prolyl endopeptidase. Immediately after the addition of PEP, the mixture is stirred with a pestle under a hot air current (40° C.) and then placed in a desiccator under vacuum overnight to remove the solvent. The resulting solid-mass is pulverized with a pestle and kneaded with 30 mg of sodium bicarbonate and a small amount of 70% ethanol. The mixture is then divided and shaped into pills of about 2 mm size and thoroughly dried. The dried pills are given a coating of hydroxypropylmethylcellulose phthalate (HP-55) to obtain an enteric formulation.

Example 9

Diagnostic Methods

The 33-mer peptide ((SEQ ID NO:12) LQLQPF-PQPQLPYPQPQLPYPQPQLP YPQPQPF) and its deamidated derivatives that are formed by the action of tissue transglutaminase are useful diagnostic reagents for the detection of Celiac Sprue. The enzyme tTGase deamidates the 33-mer at least at the underlined positions shown in the following sequence: (SEQ ID NO:12) LQLQPFPQP QLPYPQPQLPYPQPQLPYPQPQPF, and deamidated counterparts of the 33-mer are important reagents of the present invention. Such deamidated counterparts may comprise one, two or more deamidated glutamine (Q) residues.

Oligoeptide analogs of the oligopeptides described by amino acid sequence herein are also included. Such analogs contain at least one difference in amino acid sequence between the analog and native antigenic peptide. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included with the scope of the present invention are amino acids that have been altered by chemical means such as methylation (e.g., α-methylvaline), deamidation, amidation of the C-terminal amino acid by an alkylamine such as ethylamine, ethanolamine, and ethylene diamine, and acylation or methylation of an amino acid side chain function (e.g., acylation of the epsilon amino group of lysine), deimination of arginine to citrulline, isoaspartylation, or phosphorylation on serine, threonine, tyrosine or histidine residues. Candidate oligopeptide analogs may be screened for utility in a diagnostic method of the invention by an assay measuring competitive binding to antibodies, T cell receptor, etc. Those analogs that inhibit binding of the native peptides are useful diagnostic reagents. Oligopeptides and oligopeptide analogs may be synthesized by standard chemistry techniques, including synthesis by automated procedure.

Monoclonal antibodies are provided by the invention, which react specifically with this peptide and its deamidated derivatives. Methods of producing antibodies are well known in the art. Polyclonal antibodies are raised by a standard protocol, for example by injecting a production animal with an antigenic composition, formulated as described above. See, e.g., Harlow and Lane, Antibodies: A Laboratory Manual, Cold Spring Harbor Laboratory, 1988. When a peptide immunogen is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). Polyclonal antibodies specific for the polypeptide may then be purified from such antisera by, for example, affinity chromatography using the polypeptide coupled to a suitable solid support. Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line. Many such cell lines (such as myelomas) are known to those skilled in the art. In addition, antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

The 33mer peptide is exceptionally resistant toward gastrointestinal proteolysis, thereby allowing the peptide to persist as it travels through the intestinal tract. Also, this peptide includes multiple copies of immunogenic epitopes from gliadin that are recognized by antibodies in most Celiac patients. Because multivalent epitopes are known to elicit an especially vigorous immune response (e.g. Boniface et al., 1998, *Immunity* 9: 459), the 33-mer and its deamidated derivatives have inflammatory properties in the Celiac intestine, even at low doses. Moreover, as tTGase is known to become transiently linked to its substrate, the present invention provides fusion proteins in which all or a portion of a mammalian tTGase, including but not limited to human, bovine, equine, and porcine tTGase, is linked, usually covalently, to the 33-mer of the invention, wherein the linkage site is at a site for eventual deamidation. This fusion protein of the invention is a highly potent stimulator of T cells from Celiac Sprue patients in that the fusion protein exactly mimics the complexes formed in Celiac Sprue patients and is recognized by the anti-tTGase antibodies and by T cells in those patients.

In one embodiment, the present invention provides a diagnostic for Celiac Sprue that is a urine test. It is well known that the permeability of the small intestine increases during active Celiac Sprue and reduces again when a strict gluten-free diet is followed (e.g. Johnston et al., 2001, *Lancet* 358: 259). As the 33-mer peptide traverses the small intestine, a small amount of the peptide derived from a test meal will induce leakiness, and in turn be transported across the epithelial layer, and passed into urine. Given its proteolytic resistance, this peptide will emerge in the urine, and can be detected by standard analytical procedures such as LC-tandem mass spectrometry or an antibody-based diagnostic test. Presence of the peptide in the urine is diagnostic for Celiac Sprue. The sensitivity of this diagnostic procedure could be increased through the use of $^{13}C$ or other labeled peptide. Moreover, in current practice, an individual suspected of having Celiac Sprue is typically placed on a gluten-free diet and then challenged with gluten some weeks later to see if symptoms reappear. The diagnostic tests of the present invention can be used upon the physician's first suspicion that an individual is suffering from Celiac Sprue, thereby avoiding the harmful effects of placing that individual back on a gluten-containing diet and re-inducing the disease symptoms.

In one embodiment, the present invention provides a diagnostic for Celiac Sprue that is a blood test. As discussed above, the 33-mer can also be detected in peripheral blood samples, when ingested in small quantities by Celiac Sprue individuals or at the time of an initial screening at a physician's office.

In one embodiment, the present invention provides a diagnostic for Celiac Sprue that is based on intestinal biopsy staining. Labeled forms of the 33-mer provided by the present invention (e.g. peptide conjugated to a fluorescent or other label) can be used to stain intestinal biopsy samples from Celiac Sprue patients. Due to their multivalency and anticipated high affinity for antigen presenting cells and, in turn, inflammatory T cells, such peptides can be used to detect the presence of disease specific immune cells in biopsy tissue. Of particular relevance is the use of such assays to identify patients whose disease is in remission as a result of a gluten-free diet. As noted above, current clinical practices are unable to diagnose a patient when he or she is on a gluten-free diet, and require that the patient be subjected to the discomfort of a gluten containing diet for a significant time period.

In one embodiment, the present invention provides a diagnostic for Celiac Sprue in which labeled forms of the 33-mer are used to detect disease specific immune cells in peripheral blood.

In one embodiment, the present invention provides a diagnostic for Celiac Sprue that is based on an oral mucosa challenge. Inflammatory peptides from gluten can be used to detect Celiac Sprue by local challenge on oral mucosa of patients (see Lahteenoja et al., 2000, *Am. J. Gastroenterol.* 95: 2880). Given the proteolytic resistance and immunogenicity of the 33-mer, the 33-mer can be especially useful in a diagnostic procedure in which the peptide is contacted with the oral mucosa of an individual, and a diagnosis of Celiac Sprue is made if inflammation results. Again, a particular advantage of such a test would be its sensitivity to detect a patient whose disease is in remission due to a gluten-free diet.

In one embodiment, the diagnosis involves detecting the presence of T cells reactive with the 33-mer or a deamidated counterpart thereof, or a tTGase-linked counterpart thereof in a tissue, bodily fluid, or stool of an individual. T cells can also be detected by proliferation in response to exposure to an antigen provided by the present invention and presented by autologous or suitable allogeneic antigen presenting cells. The presence of such reactive T cells indicates the presence of an on-going immune response. The antigen used in the assays may be the complete 33-mer, deamidated counterpart, or a tTGase-linked counterpart; or peptides derived therefrom, usually such peptides will be at least about 12 amino acids in length. A subset of peptides may be prepared, or a mixture that encompasses the complete sequence. Overlapping peptides may be generated, where each peptide is frameshifted from 1 to 5 amino acids, thereby generating a set of epitopes.

Quantitation of T cells can be performed by determining cognate binding of the T cell receptor present on a cell, to an MHC/peptide complex, e.g. using Class I or Class II MHC tetramers (see Altman et al. *Science* (1996) 274: 94-96;

McMichael and O'Callaghan *J Exp Med*. (1998) 187: 1367-1371). MHC Tetramers are complexes of the soluble fragments of four MHC molecules, which are associated with a specific peptide. The tetramer may be bound to a fluorochromes or other detectable label. (see Ogg et al. (1998) *Curr Opin Immunol*. 10: 393-396). The tetramer may comprise a soluble fragment of HLA-DQ2 [DQ(a1*0501, b1*02)] and/or DQ8 [DQ(a1*0301, b1*0302)] molecule, or other MHC types appropriate for the individual being tested.

The diagnosis may determine the level of reactivity, e.g. based on the number of reactive T cells found in a sample, as compared to a negative control from a naive host, or standardized to a data curve obtained from one or more positive controls. In addition to detecting the qualitative and quantitative presence of antigen reactive T cells, the T cells may be typed as to the expression of cytokines known to increase or suppress inflammatory responses. While not necessary for diagnostic purposes, it may also be desirable to type the epitopic specificity of the reactive T cells, particularly for use in therapeutic administration of peptides.

In another embodiment, the diagnosis involves detecting the presence of an antibody, reactive with the 33-mer or a deamidated counterpart thereof, or a tTGase-linked counterpart thereof in a tissue, bodily fluid, or stool of an individual. An antibody is detected by, for example, an agglutination assay using an antigen provided by the present invention. Samples may be obtained from patient tissue, which may be a mucosal tissue, including but not limited to oral, nasal, lung, and intestinal mucosal tissue, a bodily fluid, e.g. blood, sputum, urine, phlegm, lymph, and tears. Also included in the term are derivatives and fractions of such fluids. Blood samples and derivatives thereof are of particular interest. One advantage of the present invention is that the antigens provided are such potent antigens that the diagnostic methods of the invention can be employed with samples (tissue, bodily fluid, or stool) in which a Celiac Sprue diagnostic antibody, peptide, or T cell is present in very low abundance. This allows the methods of the invention to be practiced in ways that are much less invasive, much less expensive, and much less harmful to the Celiac Sprue individual.

Measuring the concentration of specific antibodies in a sample or fraction thereof may be accomplished by a variety of specific assays, as are known in the art. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In one embodiment, a conventional sandwich type assay is used. A sandwich assay is performed by first attaching the peptide to an insoluble surface or support. The peptide may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently.

In some cases, a competitive assay will be used. In addition to the patient sample, a competitor to the antibodies is added to the reaction mix. The competitor and the antibodies compete for binding to the antigenic peptide. Usually, the competitor molecule will be labeled and detected as previously described, where the amount of competitor binding will be proportional to the amount of antibodies present. The concentration of competitor molecule will be from about 10 times the maximum anticipated antibodies concentration to about equal concentration in order to make the most sensitive and linear range of detection.

An alternative protocol is to provide anti-patient antibodies bound to the insoluble surface. After adding the sample and washing away non-specifically bound proteins, one or a combination of the test antigens are added, where the antigens are labeled, so as not to interfere with binding to the antibodies. Conveniently, fused proteins may be employed, where the peptide sequence is fused to an enzyme sequence, e.g.—galactosidase.

The subject methods are useful not only for diagnosing Celiac Sprue individuals but also for determining the efficacy of prophylactic or therapeutic methods for Celiac Sprue as well as the efficacy of food preparation or treatment methods aimed at removing glutens or similar substances from food sources. Thus, a Celiac Sprue individual efficaciously treated with a prophylactic or therapeutic drug or other therapy for Celiac Sprue tests more like a non-Celiac Sprue individual with the methods of the invention. Likewise, the antibodies or T cell responders, e.g. T cell lines, of the invention that detect the toxic gluten oligopeptides of the invention are useful in detecting gluten and gluten-like substances in food and so can be used to determine whether a food treated to remove such substances has been efficaciously treated.

These and other diagnostic methods of the invention can be practiced using the novel peptides and antibodies provided by the invention.

All publications, patents, and patent applications cited in this specification are herein incorporated by reference as if each individual publication, patent, or patent application were specifically and individually indicated to be incorporated by reference.

The present invention has been described in terms of particular embodiments found or proposed by the inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in methods, structures, and compounds without affecting the biological action in kind or amount. All such modifications are intended to be included within the scope of the appended claims.

What is claimed is:

1. A method for treating a foodstuff comprising wheat gluten proteins, said method comprising contacting said foodstuff comprising wheat gluten proteins in vitro with a glutenase, wherein said glutenase has a $k_{cat}/K_m$ of at least 250 $s^{-1}/m^{-1}$ for cleaving one or both of the oligopeptides of SEQ ID NO:3 and SEQ ID NO:12 under physiologic conditions into fragments shorter than 8 amino acids;

to prepare a pre-treated foodstuff that is less toxic to a Celiac sprue and/or dermatitis herpetiformis patient, relative to the untreated foodstuff, and contains enzymatically active glutenase when ingested by said patient.

2. The method of claim 1, wherein the glutenase is a peptidase selected from the group consisting of a prolyl endopeptidase (PEP); a PEP homolog; an endoproteinase from a developing grain of a gluten-containing cereal; a brush border enzyme; a dipeptidyl carboxypeptidase; and a dipeptidyl peptidase 4.

3. The method of claim 2, wherein the peptidase is selected from the group consisting of a PEP from *Flavobacterium meningosepticum, Aeromonas hydrophila, Sphingomonas capsulata*, and *Lactobacilli*; a dipeptidyl carboxypeptidase from *Pseudomonas, Streptomyces*, and *Aspergilli*; a dipeptidyl peptidase IV from *Prevotella albensis, Porphyromonas gingivalis, Lactobacillus helveticus*, and *Lactococcus*; a cysteine proteinase B from *Hordeum vulgare*; a PEP homolog from *Aeromonas punctata, Novosphingobium capsulatum, Pyrococcus furiosus, E. coli*, and *Myxococcus xanthus*; and an endoproteinase from a developing grain of wheat, barley, and rye.

4. The method according to claim 1, wherein said glutenase is formulated with a pharmaceutically acceptable excipient.

5. The method according to claim 1, wherein said glutenase is stable to acid conditions in the stomach of said patient.

6. The method according to claim 1, wherein said glutenase is contained in a formulation that comprises an enteric coating.

7. The method of claim 1, wherein the glutenase is formulated in a solid preparation.

8. A method for treating a gluten-containing foodstuff to render said foodstuff less toxic to a Celiac Sprue and/or dermatitis herpetiformis patient, said method comprising:

contacting said foodstuff in vitro with a glutenase, wherein said glutenase has a $k_{cat}/K_m$ of at least 250 $s^{-1}/m^{-1}$ for cleaving one or both of the oligopeptides of SEQ ID NO:3 and SEC) ID NO:12 under physiologic conditions into fragments shorter than 8 amino acids;

to form a pre-treated foodstuff that is then ingested by said patient, wherein said pre-treated foodstuff contains enzymatically active glutenase during ingestion, and wherein immunogenic gluten peptides in gluten-containing foodstuffs are cleaved into non-toxic fragments.

9. The method of claim 8, wherein said glutenase is a peptidase selected from the group consisting of a prolyl endopeptidase (PEP); a PEP homolog; an endoproteinase from a developing grain of a gluten-containing cereal; a brush border enzyme; a dipeptidyl carboxypeptidase; and a dipeptidyl peptidase 4.

10. The method of claim 9, wherein said peptidase is selected from the group consisting of a PEP from *Flavobacterium meningosepticum, Aeromonas hydrophila, Sphingomonas capsulata*, and *Lactobacilli*; a dipeptidyl carboxypeptidase from *Pseudomonas, Streptomyces*, and *Aspergilli*; a dipeptidyl peptidase IV from *Prevotella albensis, Porphyromonas gingivalis, Lactobacillus helveticus*, and *Lactococcus*; a cysteine proteinase B from *Hordeum vulgare*; a PEP homolog from *Aeromonas punctata, Novosphingobium cap-*

*sulatum, Pyrococcus furiosus, E. coli,* and *Myxococcus xanthus*; and an endoproteinase from a developing grain of wheat, barley, and rye.

11. The method according to claim 8, wherein said glutenase is formulated with a pharmaceutically acceptable excipient.

12. The method according to claim 8, wherein said glutenase is stable to acid conditions in the stomach of said patient.

13. The method according to claim 8, wherein said glutenase is contained in a formulation that comprises an enteric coating.

14. The method of claim 8, wherein the gluten-containing foodstuff comprises wheat gluten proteins.

15. The method of claim 8, wherein the glutenase is formulated in a solid preparation.

16. A method for treating a foodstuff comprising wheat gluten protein to render said foodstuff less toxic to a Celiac Sprue and/or dermatitis herpetiformis patient, said method comprising:

contacting said foodstuff comprising wheat gluten protein in vitro with a prolyl endopeptidase, wherein said prolyl endopeptidase has a $k_{cat}/K_m$ of at least 250 $s^{-1}/m^{-1}$ for cleaving one or both of the oligopeptides of SEQ ID NO:3 and SEQ ID NO:12 under physiologic conditions into fragments shorter than 8 amino acids;

to form a pre-treated foodstuff that contains enzymatically active prolyl endopeptidase; and administering said pre-treated foodstuff to said patient, wherein immunogenic gluten peptides in the wheat gluten proteins are cleaved into non-toxic fragments.

17. The method of claim 16, wherein the patient has celiac sprue and exhibits one or more symptoms from the group consisting of fatigue, chronic diarrhea, malabsorption of nutrients, weight loss, abdominal distension, and anemia.

18. The method of claim 16, wherein the patient has dermatitis herpetiformis that manifests as clusters of intensely pruritic vesicles, papules, and urticaria-like lesions on said patient's skin.

19. The method of claim 16, wherein the glutenase is formulated in a solid preparation.

* * * * *

SEQUENCE LISTING

<160> NUMBER OF SEQ ID NOS: 32

<210> SEQ ID NO 1
<211> LENGTH: 12
<212> TYPE: PRT
<213> ORGANISM: Triticum aestivum

<400> SEQUENCE: 1

Gln Leu Gln Pro Phe Pro Gln Pro Gln Leu Pro Tyr
1               5                   10

<210> SEQ ID NO 2
<211> LENGTH: 12
<212> TYPE: PRT
<213> ORGANISM: Triticum aestivum
<220> FEATURE:
<221> NAME/KEY: PYRROLIDONE CAR
<222> LOCATION: (1)...(1)
<223> OTHER INFORMATION: N terminal pyroglutaminate

<400> SEQUENCE: 2

Gln Leu Gln Pro Phe Pro Gln Pro Gln Leu Pro Tyr
1               5                   10

<210> SEQ ID NO 3
<211> LENGTH: 14
<212> TYPE: PRT
<213> ORGANISM: Triticum aestivum

<400> SEQUENCE: 3

Pro Gln Pro Gln Leu Pro Tyr Pro Gln Pro Gln Leu Pro Tyr
1               5                   10

<210> SEQ ID NO 4
<211> LENGTH: 13
<212> TYPE: PRT
<213> ORGANISM: Triticum aestivum

<400> SEQUENCE: 4

Pro Gln Pro Gln Leu Pro Tyr Pro Gln Pro Gln Leu Pro
1               5                   10

<210> SEQ ID NO 5
<211> LENGTH: 11
<212> TYPE: PRT
<213> ORGANISM: Triticum aestivum

<400> SEQUENCE: 5

Gln Leu Gln Pro Phe Pro Gln Pro Gln Leu Pro
1               5                   10

<210> SEQ ID NO 6
<211> LENGTH: 11
<212> TYPE: PRT
<213> ORGANISM: Triticum aestivum

<400> SEQUENCE: 6

Gln Pro Gln Phe Pro Gln Pro Gln Leu Pro Tyr
1               5                   10

<210> SEQ ID NO 7
<211> LENGTH: 9
<212> TYPE: PRT
<213> ORGANISM: Triticum aestivum

<400> SEQUENCE: 7

Gln Pro Phe Pro Gln Pro Gln Leu Pro
1               5

<210> SEQ ID NO 8
<211> LENGTH: 6
<212> TYPE: PRT

-continued

```
<213> ORGANISM: Triticum aestivum

<400> SEQUENCE: 8

Pro Gln Pro Gln Leu Pro
1               5

<210> SEQ ID NO 9
<211> LENGTH: 13
<212> TYPE: PRT
<213> ORGANISM: Triticum aestivum

<400> SEQUENCE: 9

Arg Arg Leu Ile Glu Asp Asn Glu Tyr Thr Ala Arg Gly
1               5                   10

<210> SEQ ID NO 10
<211> LENGTH: 10
<212> TYPE: PRT
<213> ORGANISM: Triticum aestivum

<400> SEQUENCE: 10

Gln Pro Phe Pro Gln Pro Gln Leu Pro Tyr
1               5                   10

<210> SEQ ID NO 11
<211> LENGTH: 7
<212> TYPE: PRT
<213> ORGANISM: Triticum aestivum

<400> SEQUENCE: 11

Phe Pro Gln Pro Gln Leu Pro
1               5

<210> SEQ ID NO 12
<211> LENGTH: 33
<212> TYPE: PRT
<213> ORGANISM: triticum aestivum

<400> SEQUENCE: 12

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
                20                  25                  30

Phe

<210> SEQ ID NO 13
<211> LENGTH: 10
<212> TYPE: PRT
<213> ORGANISM: Triticum aestivum

<400> SEQUENCE: 13

Gln Pro Gln Gln Ser Phe Pro Gln Gln Gln
1               5                   10

<210> SEQ ID NO 14
<211> LENGTH: 12
<212> TYPE: PRT
<213> ORGANISM: triticum aestivum

<400> SEQUENCE: 14

Gln Leu Gln Pro Phe Pro Gln Pro Glu Leu Pro Tyr
1               5                   10
```

```
<210> SEQ ID NO 15
<211> LENGTH: 14
<212> TYPE: PRT
<213> ORGANISM: Triticum aestrivum

<400> SEQUENCE: 15

Pro Gln Pro Glu Leu Pro Tyr Pro Gln Pro Glu Leu Pro Tyr
1               5                   10

<210> SEQ ID NO 16
<211> LENGTH: 10
<212> TYPE: PRT
<213> ORGANISM: Triticum aestivum

<400> SEQUENCE: 16

Gln Pro Gln Gln Ser Phe Pro Glu Gln Gln
1               5                   10

<210> SEQ ID NO 17
<211> LENGTH: 13
<212> TYPE: PRT
<213> ORGANISM: Triticum aestivum

<400> SEQUENCE: 17

Pro Gln Pro Glu Leu Pro Tyr Pro Gln Pro Gln Leu Pro
1               5                   10

<210> SEQ ID NO 18
<211> LENGTH: 14
<212> TYPE: PRT
<213> ORGANISM: Triticum aestivum

<400> SEQUENCE: 18

Pro Gln Pro Glu Leu Pro Tyr Pro Gln Pro Gln Pro Leu Pro
1               5                   10

<210> SEQ ID NO 19
<211> LENGTH: 5
<212> TYPE: PRT
<213> ORGANISM: Artificial Sequence
<220> FEATURE:
<223> OTHER INFORMATION: Peptide motif

<400> SEQUENCE: 19

Gly Pro Leu Gly Pro
1               5

<210> SEQ ID NO 20
<211> LENGTH: 9
<212> TYPE: PRT
<213> ORGANISM: Artificial Sequence
<220> FEATURE:
<223> OTHER INFORMATION: T cell epitope

<400> SEQUENCE: 20

Pro Phe Pro Gln Pro Gln Leu Pro Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: T cell epitope

<400> SEQUENCE: 21
```

```
Pro Gln Pro Gln Leu Pro Tyr Pro Gln
  1               5
```

<210> SEQ ID NO 22
<211> LENGTH: 9
<212> TYPE: PRT
<213> ORGANISM: Artificial Sequence
<220> FEATURE:
<223> OTHER INFORMATION: T cell epitope

<400> SEQUENCE: 22

```
Pro Tyr Pro Gln Pro Gln Leu Pro Tyr
  1               5
```

<210> SEQ ID NO 23
<211> LENGTH: 8
<212> TYPE: PRT
<213> ORGANISM: Artificial Sequence
<220> FEATURE:
<223> OTHER INFORMATION: Digestion product

<400> SEQUENCE: 23

```
Trp Gln Ile Pro Glu Gln Ser Arg
  1               5
```

<210> SEQ ID NO 24
<211> LENGTH: 34
<212> TYPE: PRT
<213> ORGANISM: Triticum aestivum

<400> SEQUENCE: 24

```
Gln Pro Gln Pro Phe Pro Pro Gln Leu Pro Tyr Pro Gln Thr Gln Pro
  1               5                  10                  15

Phe Pro Pro Gln Gln Pro Tyr Pro Gln Pro Gln Pro Tyr Pro Gln
                 20                  25                  30

Pro Gln
```

<210> SEQ ID NO 25
<211> LENGTH: 35
<212> TYPE: PRT
<213> ORGANISM: Triticum aestivum

<400> SEQUENCE: 25

```
Gln Gln Gln Pro Phe Pro Gln Gln Pro Ile Pro Gln Gln Pro Gln Pro
  1               5                  10                  15

Tyr Pro Gln Gln Pro Gln Pro Tyr Pro Gln Gln Pro Phe Pro Pro Gln
                 20                  25                  30

Gln Pro Phe
         35
```

<210> SEQ ID NO 26
<211> LENGTH: 30
<212> TYPE: PRT
<213> ORGANISM: Triticum aestivum

<400> SEQUENCE: 26

```
Gln Pro Phe Pro Gln Pro Gln Gln Thr Phe Pro Gln Gln Pro Gln Leu
  1               5                  10                  15

Pro Phe Pro Gln Gln Pro Gln Gln Pro Phe Pro Gln Pro Gln
                 20                  25                  30
```

<210> SEQ ID NO 27
<211> LENGTH: 30

```
<212> TYPE: PRT
<213> ORGANISM: Triticum aestivum

<400> SEQUENCE: 27

Gln Pro Phe Pro Gln Pro Gln Gln Pro Thr Pro Ile Gln Pro Gln Gln
 1               5                  10                  15

Pro Phe Pro Gln Arg Pro Gln Gln Pro Phe Pro Gln Pro Gln
            20                  25                  30

<210> SEQ ID NO 28
<211> LENGTH: 7
<212> TYPE: PRT
<213> ORGANISM: Artificial Sequence
<220> FEATURE:
<223> OTHER INFORMATION: synthetic substrates
<220> FEATURE:
<221> NAME/KEY: VARIANT
<222> LOCATION: (1)...(1)
<223> OTHER INFORMATION: Abz modified Glutamine
<220> FEATURE:
<221> NAME/KEY: VARIANT
<222> LOCATION: (6)...(6)
<223> OTHER INFORMATION: NO2 modified Tyrosine

<400> SEQUENCE: 28

Gln Pro Gln Gln Pro Tyr Asp
 1               5

<210> SEQ ID NO 29
<211> LENGTH: 6
<212> TYPE: PRT
<213> ORGANISM: Artificial Sequence
<220> FEATURE:
<223> OTHER INFORMATION: synthetic substrates
<220> FEATURE:
<221> NAME/KEY: VARIANT
<222> LOCATION: (1)...(1)
<223> OTHER INFORMATION: Abz modified Glutamine
<220> FEATURE:
<221> NAME/KEY: VARIANT
<222> LOCATION: (4)...(4)
<223> OTHER INFORMATION: NO2 modified Tyrosine

<400> SEQUENCE: 29

Gln Leu Pro Tyr Pro Gln
 1               5

<210> SEQ ID NO 30
<211> LENGTH: 7
<212> TYPE: PRT
<213> ORGANISM: Artificial Sequence
<220> FEATURE:
<223> OTHER INFORMATION: synthetic substrates
<220> FEATURE:
<221> NAME/KEY: VARIANT
<222> LOCATION: (1)...(1)
<223> OTHER INFORMATION: Abz modified Proline
<220> FEATURE:
<221> NAME/KEY: VARIANT
<222> LOCATION: (7)...(7)
<223> OTHER INFORMATION: NO2 modified Tyrosine

<400> SEQUENCE: 30

Pro Tyr Pro Gln Pro Gln Tyr
 1               5

<210> SEQ ID NO 31
<211> LENGTH: 13
<212> TYPE: PRT
<213> ORGANISM: Artificial Sequence
```

-continued

```
<220> FEATURE:
<223> OTHER INFORMATION: synthetic substrates
<220> FEATURE:
<221> NAME/KEY: VARIANT
<222> LOCATION: (4)...(4)
<223> OTHER INFORMATION: Abz modified Lysine
<220> FEATURE:
<221> NAME/KEY: VARIANT
<222> LOCATION: (7)...(7)
<223> OTHER INFORMATION: NO2 modified Tyrosine

<400> SEQUENCE: 31

Pro Gln Pro Lys Leu Pro Tyr Pro Gln Pro Gln Leu Pro
1               5                   10

<210> SEQ ID NO 32
<211> LENGTH: 13
<212> TYPE: PRT
<213> ORGANISM: Artificial Sequence
<220> FEATURE:
<223> OTHER INFORMATION: synthetic substrates
<220> FEATURE:
<221> NAME/KEY: VARIANT
<222> LOCATION: (7)...(7)
<223> OTHER INFORMATION: NO2 modified Tyrosine
<220> FEATURE:
<221> NAME/KEY: VARIANT
<222> LOCATION: (11)...(11)
<223> OTHER INFORMATION: Abz modified Lysine

<400> SEQUENCE: 32

Pro Gln Pro Gln Leu Pro Tyr Pro Gln Pro Lys Leu Pro
1               5                   10
```